United States Patent
Usuda

(10) Patent No.: US 12,062,446 B2
(45) Date of Patent: Aug. 13, 2024

(54) LEARNING DEVICE, LEARNING METHOD, AND LEARNED MODEL

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 259 days.

(21) Appl. No.: 17/082,028

(22) Filed: Oct. 28, 2020

(65) Prior Publication Data

US 2021/0142901 A1 May 13, 2021

(30) Foreign Application Priority Data

Nov. 11, 2019 (JP) ................................ 2019-203965

(51) Int. Cl.

| | |
|---|---|
| *G16H 50/20* | (2018.01) |
| *A61B 8/08* | (2006.01) |
| *A61B 8/12* | (2006.01) |
| *G06F 18/21* | (2023.01) |
| *G06K 9/62* | (2022.01) |
| *G06K 9/78* | (2006.01) |

(Continued)

(52) U.S. Cl.
CPC ............... *G16H 50/20* (2018.01); *A61B 8/12* (2013.01); *A61B 8/5207* (2013.01); *G06F 18/21* (2023.01);
(Continued)

(58) Field of Classification Search
CPC .......... G16H 50/20; G16H 30/40; A61B 8/12; A61B 8/5207; A61B 8/5223; A61B 8/54;
(Continued)

(56) References Cited

U.S. PATENT DOCUMENTS 10,769,502 B1* 9/2020 Berg ....................... G06F 16/51
10,860,930 B2 12/2020 Shiratani
(Continued)

FOREIGN PATENT DOCUMENTS

| JP | H06233761 | 8/1994 |
|---|---|---|
| JP | 2010069018 | 4/2010 |

(Continued)

OTHER PUBLICATIONS

"Office Action of Japan Counterpart Application" with English translation thereof, dated Nov. 29, 2022, p. 1-p. 8.

*Primary Examiner* — Alexei Bykhovski
(74) *Attorney, Agent, or Firm* — JCIPRNET

(57) ABSTRACT

Provided are a learning device, a learning method, and a learned model capable of allowing an operator to ascertain what part inside a body of a subject is observed in the middle of examination by medical equipment.
In a learning device, a learning method and, a learned model, an image acquisition unit acquires a medical image of an observation target part inside the body of the subject in each of a plurality of observation steps in which an observation order of the observation target part is determined, a step prediction unit outputs a prediction step predicting an observation step corresponding to the medical image from the medical image based on a learning result in each observation step, a step comparison unit compares the prediction step with a ground truth step corresponding to the prediction step in each observation step, and a learning controller makes the step prediction unit learn a relationship between the medical image and the prediction step based on a result of comparison by the step comparison unit in each observation step such that the prediction step becomes close to the ground truth step.

12 Claims, 10 Drawing Sheets

(51) Int. Cl.
  *G06V 10/44*  (2022.01)
  *G06V 10/764*  (2022.01)
  *G16H 30/40*  (2018.01)

(52) U.S. Cl.
  CPC .......... *G06V 10/454* (2022.01); *G06V 10/764* (2022.01); *G16H 30/40* (2018.01); *G06V 2201/03* (2022.01)

(58) Field of Classification Search
  CPC .. G06K 9/6217; G06V 10/10; G06V 2201/03; G06V 10/764; G06V 10/454; G06F 18/21
  See application file for complete search history.

(56) References Cited

U.S. PATENT DOCUMENTS

| | | | |
|---|---|---|---|
| 11,386,288 B2 | 7/2022 | Yamamoto et al. | |
| 2010/0081931 A1* | 4/2010 | Destrempes | G06T 7/12 |
| | | | 382/128 |
| 2017/0086785 A1* | 3/2017 | Bjaerum | A61B 8/4444 |
| 2020/0311490 A1* | 10/2020 | Lee | G01T 1/17 |
| 2020/0410677 A1 | 12/2020 | Keshwani | |
| 2021/0004957 A1* | 1/2021 | Aalamifar | G06T 7/10 |

FOREIGN PATENT DOCUMENTS

| | | |
|---|---|---|
| JP | 2018139848 | 9/2018 |
| JP | 2019159654 | 9/2019 |
| JP | 2019180866 | 10/2019 |
| WO | 2017175282 | 10/2017 |
| WO | 2019156706 | 8/2019 |
| WO | 2019176806 | 9/2019 |
| WO | 2019208793 | 10/2019 |

\* cited by examiner

LEARNING DEVICE, LEARNING METHOD, AND LEARNED MODEL

CROSS-REFERENCE TO RELATED APPLICATIONS

The present application claims priority under 35 U.S.C. § 119 to Japanese Patent Application No. 2019-203965, filed on Nov. 11, 2019. The above application is hereby expressly incorporated by reference, in its entirety, into the present application.

BACKGROUND OF THE INVENTION

1. Field of the Invention

The present invention relates to a learning device, a learning method, and a learned model that learn a relationship between a medical image and a prediction step on a plurality of medical images, and output a prediction step predicting an observation step corresponding to a medical image from the medical image based on a learning result.

2. Description of the Related Art

For example, an ultrasound endoscope system, for the primary purpose of observation of a pancreas, a gallbladder, or the like using a trans-digestive tract, an ultrasound endoscope having an endoscope observation portion and an ultrasound observation portion at a distal end is inserted into a digestive tract of a subject, and an endoscope image inside the digestive tract and an ultrasound image of a part outside a wall of the digestive tract are captured.

In the ultrasound endoscope system, an observation target adjacent part inside the digestive tract is irradiated with illumination light from an illumination part provided at the distal end of the ultrasound endoscope, reflected light of illumination light is received by an imaging part provided at the distal end of the ultrasound endoscope, and an endoscope image is generated from an imaging signal of reflected light. Furthermore, ultrasonic waves are transmitted and received to and from an observation target part, such as an organ outside the wall of the digestive tract, by a plurality of ultrasound transducers provided at the distal end of the ultrasound endoscope, and an ultrasound image is generated from reception signals of the ultrasonic waves.

Here, examples of the related art having relation to the invention are JP1994-233761A (JP-H06-233761A) and JP2010-069018A.

JP1994-233761A (JP-H06-233761A) describes that an intended part in an image of a diagnosis part inside a subject is roughly extracted, global information for recognizing the intended part is predicted using a neural network, a contour of the intended part is recognized using the global information, and a recognition result is displayed along with an original image.

JP2010-069018A describes that position and alignment data of a distal end portion of an ultrasound endoscope is generated based on an electric signal from a coil, insertion shape data for indicating an insertion shape of the ultrasound endoscope is generated from the position and alignment data, a guide image is generated by combining the insertion shape data with three-dimensional biological tissue model data of a tissue structure of an organ group or the like of a subject, and a video signal of a composite image, in which an ultrasound image and the guide image are composed, is generated and displayed on a monitor.

SUMMARY OF THE INVENTION

An operator (user) that handles medical equipment, such as in-vitro ultrasound equipment, endoscope, or an ultrasound endoscope, views an image captured by the medical equipment and operates the medical equipment while presuming which part inside a body of a subject is observed at this moment. However, while examination is executed using the medical equipment, it is difficult for the operator to ascertain whether or not an intended part, such as an organ, can be observed or where the intended part is observed from at this moment. For example, in a case of an endoscope, since there is an imaging system in a distal end portion of a scope inserted into the body of the subject, the operator does not know a position where the distal end portion of the scope is present inside the body of the subject. Furthermore, in a case of an ultrasound endoscope, since the ultrasound endoscope is medical equipment in which an imaging part having an ultrasound transducer cannot be visually confirmed and a captured ultrasound image is hardly interpreted, there are many cases where an intended part is missed or the intended part is not reached.

Accordingly, it is effective to use a series of observation steps designed such that the operator can perform examination while following a determined observation order and can comprehensively observe intended parts. However, it is difficult for the operator to memorize all of a series of observation steps over many intended parts and to follow all observation steps while remembering during examination requiring concentration. For this reason, there is demand for a recognition technique of an observation step by image recognition.

An object of the invention is to solve the problems in the related art and to provide a learning device, a learning method, and a learned model capable of allowing an operator to ascertain which part inside a body of a subject is observed in the middle of examination by medical equipment.

In order to achieve the above-described object, an aspect of the invention provides a learning device comprising:
  an image acquisition unit that acquires a medical image of an observation target part inside a body of a subject in each of a plurality of observation steps in which an observation order of the observation target part is determined;
  a step prediction unit that outputs a prediction step predicting an observation step corresponding to the medical image from the medical image based on a learning result in each observation step;
  a ground truth step holding unit that holds a ground truth step corresponding to each observation step;
  a step comparison unit that compares the prediction step with a ground truth step corresponding to the prediction step in each observation step; and
  a learning controller that makes the step prediction unit learn a relationship between the medical image and the prediction step based on a result of comparison by the step comparison unit in each observation step such that the prediction step becomes close to the ground truth step.

It is preferable that each of the observation step, the prediction step, and the ground truth step is represented by a label number.

It is preferable that the label number is set based on the observation order of the observation target part.

It is preferable that the step prediction unit is a convolutional neural network using a loss function, and
the learning controller makes the convolutional neural network learn the relationship between the medical image and the prediction step such that an output of the loss function calculated based on a difference between the label number of the prediction step and the label number of the ground truth step is minimized.

It is preferable that the convolutional neural network outputs, as the prediction step, a discrete probability distribution vector including a plurality of elements representing a probability of the medical image being a medical image corresponding to each observation step,
the ground truth step is a discrete probability distribution vector where a probability of an element corresponding to the observation step, which is a ground truth, is 1, and a probability of an element corresponding to the observation step, which is not a ground truth, is 0, and
the loss function represents a difference between the discrete probability distribution vector of the prediction step and the discrete probability distribution vector of the ground truth step.

It is preferable that the convolutional neural network outputs a discrete probability distribution vector, in which a sum of probabilities of the plurality of elements is 1, using a softmax function.

It is preferable that the convolutional neural network outputs a discrete probability distribution vector representing a probability of each of the plurality of elements being each observation step using a sigmoid function.

It is preferable that the convolutional neural network outputs a scalar predicting a label number as the prediction step,
the ground truth step is a scalar representing the label number, and
the loss function represents a difference between the scalar of the prediction step and the scalar of the ground truth step.

It is preferable that the loss function adjusts the output of the loss function to be greater in a case where the difference is greater than a threshold value than in a case where the difference is smaller than the threshold value.

It is preferable that the plurality of observation steps include an observation step representing a state in which any observation target part is not observed.

It is preferable that, in a case of observing the medical image of the observation target part inside the body of the subject in compliance with the observation order of the observation target part, the observation step represents an order set based on the observation order of the observation target part.

It is preferable that the image acquisition unit is equipment that is inserted into a body cavity of the subject and acquires a medical image inside the body of the subject captured from the inside of the body of the subject.

It is preferable that the medical image is an ultrasound image.

It is preferable that the medical image is an ultrasound image in which an observation target part inside the body of the subject is imaged by an ultrasound endoscope.

Another aspect of the invention provides a learning method comprising:
with an image acquisition unit, acquiring a medical image of an observation target part inside a body of a subject in each of a plurality of observation steps in which an observation order of the observation target part is determined;
with a step prediction unit, outputting a prediction step predicting an observation step corresponding to the medical image from the medical image based on a learning result in each observation step;
with a step comparison unit, comparing the prediction step with a ground truth step corresponding to the prediction step in each observation step; and
with a learning controller, making the step prediction unit learn a relationship between the medical image and the prediction step based on a result of comparison by the step comparison unit such that the prediction step becomes close to the ground truth step in each observation step.

Still another aspect of the invention provides a learned model that learns a relationship between a medical image and a prediction step on a plurality of the medical images by the above-described learning method and outputs a prediction step predicting an observation step corresponding to a medical image acquired by an image acquisition unit from the medical image acquired by the image acquisition unit based on a learning result.

It is preferable that the step prediction unit, the step comparison unit, and the learning controller are hardware or a processor that executes a program, and it is preferable that the ground truth step holding unit is hardware or a memory.

In the invention, since it is possible to display information relating to the prediction step in the middle of examination by medical equipment, it is possible to allow an operator to reliably ascertain which part inside the body of the subject is observed at this moment.

DESCRIPTION OF THE PREFERRED EMBODIMENTS

An ultrasound endoscope system of an embodiment to which a learning device of the invention is applied will be described below in detail referring to a preferred embodiment shown in the accompanying drawings.

The embodiment is a representative embodiment of the invention, but is merely an example and does not limit the invention.

Outline of Ultrasound Endoscope System

Figure 1:
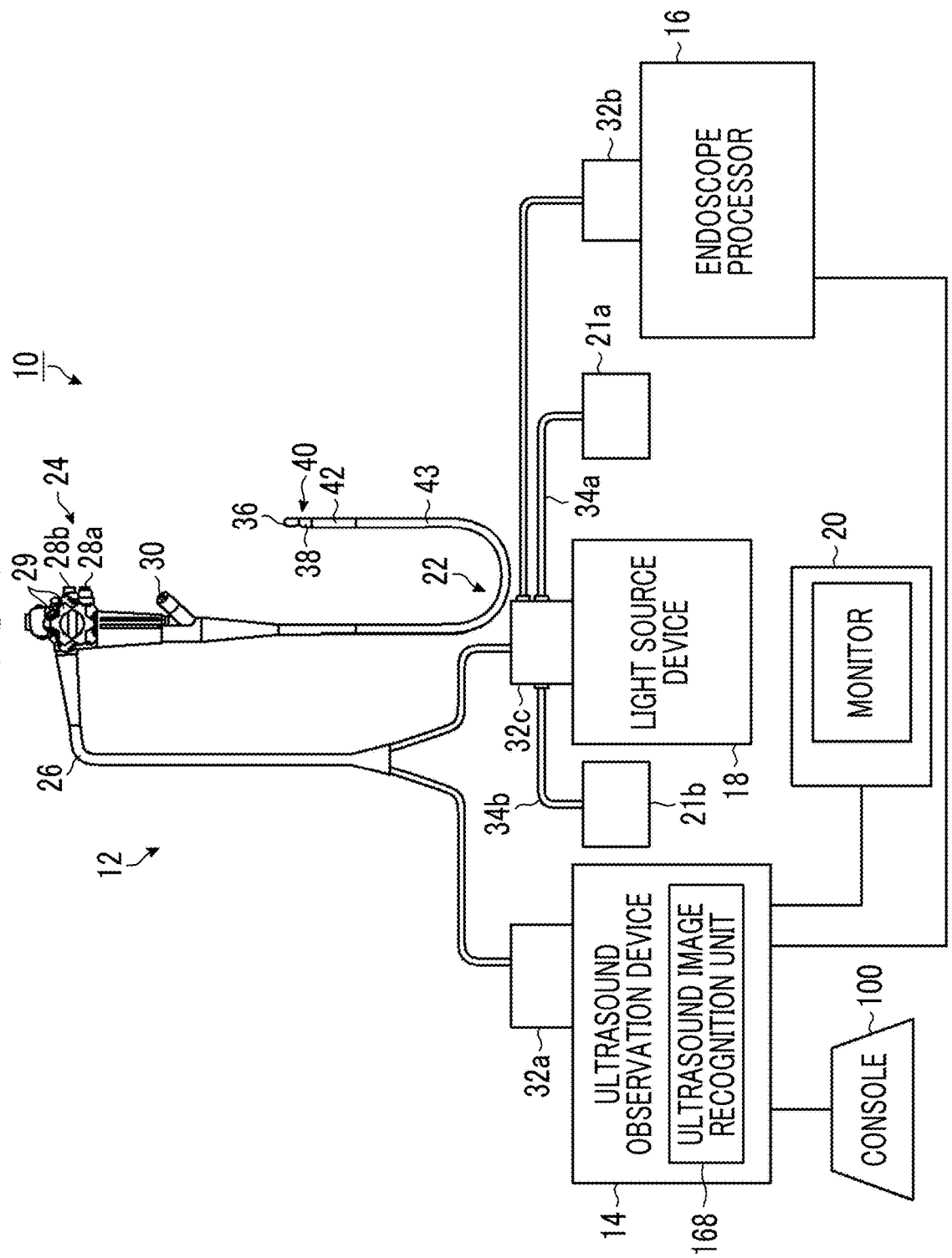
FIG. 1 is a diagram showing the schematic configuration of an ultrasound endoscope system according to an embodiment of the invention.

The outline of an ultrasound endoscope system 10 according to the embodiment will be described referring to FIG. 1. FIG. 1 is a diagram showing the schematic configuration of the ultrasound endoscope system 10.

The ultrasound endoscope system 10 is used to observe (hereinafter, referred to as ultrasound diagnosis) a state of an observation target part in a body of a patient as a subject using ultrasonic waves. Here, the observation target part is a part that is hardly examined from a body surface side of the patient, and is, for example, a part including a pancreas or a gallbladder. With the use of the ultrasound endoscope system 10, it is possible to perform ultrasound diagnosis of a state of the observation target part and the presence or absence of an abnormality by way of digestive tracts, such as esophagus, stomach, duodenum, small intestine, and large intestine, which are body cavities of the patient.

The ultrasound endoscope system 10 acquires an ultrasound image and an endoscope image, and as shown in FIG. 1, as an ultrasound endoscope 12, an ultrasound observation device 14, an endoscope processor 16, a light source device 18, a monitor 20, a water supply tank 21*a*, a suction pump 21*b*, and a console 100.

The ultrasound endoscope 12 comprises an insertion part 22 that is inserted into the body cavity of the patient, an operating part 24 that is operated by an operator (user), such as a physician or a technician, and an ultrasound transducer unit 46 (see FIGS. 2 and 3) that is attached to a distal end portion 40 of the insertion part 22. The ultrasound endoscope 12 has a plurality of ultrasound transducers 48 of an ultrasound transducer unit 46 as an ultrasound observation portion 36 at the distal end (see FIGS. 2 and 3). Furthermore, the ultrasound endoscope 12 has an illumination part including illumination windows 88 and the like and an imaging part including an observation window 82, an objective lens 84, a solid-state imaging element 86, and the like as an endoscope observation portion 38 at the distal end (see FIGS. 2 and 3). The operator acquires an endoscope image and an ultrasound image by the function of the ultrasound endoscope 12.

Here, the "endoscope image" is an image that is obtained by imaging a body cavity inner wall of the patient using an optical method. Furthermore, the "ultrasound image" is an image that is obtained by receiving reflected waves (echoes) of ultrasonic waves transmitted from the inside of the body cavity of the patient toward the observation target part and imaging reception signals.

The ultrasound endoscope 12 will be described below in detail.

The ultrasound observation device 14 is connected to the ultrasound endoscope 12 through a universal cord 26 and an ultrasound connector 32*a* provided in an end portion of the universal cord 26. The ultrasound observation device 14 performs control such that the ultrasound transducer unit 46 of the ultrasound endoscope 12 transmits the ultrasonic waves. The ultrasound observation device 14 generates the ultrasound image by imaging the reception signals when the ultrasound transducer unit 46 receives the reflected waves (echoes) of the transmitted ultrasonic waves. In other words, the ultrasound observation device 14 makes a plurality of ultrasound transducers 48 of the ultrasound transducer unit 46 transmit and receive ultrasonic waves and generates an ultrasound image from reception signals of the ultrasonic waves.

The ultrasound observation device 14 will be described below in detail.

The endoscope processor 16 is connected to the ultrasound endoscope 12 through the universal cord 26 and an endoscope connector 32*b* provided in the end portion of the universal cord 26. The endoscope processor 16 acquires image data of an observation target adjacent part imaged by the ultrasound endoscope 12 (in detail, the solid-state imaging element 86 described below) and executes predetermined image processing on the acquired image data to generate an endoscope image. In other words, the endoscope processor 16 makes the imaging part provided at the distal end of the ultrasound endoscope 12 receive reflected light of illumination light irradiated from the illumination part provided at the distal end of the ultrasound endoscope 12 and generates an endoscope image from an imaging signal of the reflected light.

Here, the "observation target adjacent part" is a portion that is at a position adjacent to the observation target part in the inner wall of the body cavity of the patient.

In the embodiment, the ultrasound observation device 14 and the endoscope processor 16 are constituted of two devices (computers) provided separately. However, the invention is not limited thereto, and both of the ultrasound observation device 14 and the endoscope processor 16 may be constituted of one device.

The light source device 18 is connected to the ultrasound endoscope 12 through the universal cord 26 and a light source connector 32*c* provided in the end portion of the universal cord 26. The light source device 18 irradiates the observation target adjacent part with white light composed of three primary color light of red light, green light, and blue light or light having a specific wavelength in imaging the observation target adjacent part using the ultrasound endoscope 12. Light irradiated from the light source device 18 propagates through the ultrasound endoscope 12 through a light guide (not shown) included in the universal cord 26 and is emitted from the ultrasound endoscope 12 (in detail, the illumination windows 88 described below). With this, the observation target adjacent part is illuminated with light from the light source device 18.

The monitor 20 is connected to the ultrasound observation device 14, and displays an ultrasound image generated by the ultrasound observation device 14, an endoscope image generated by the endoscope processor 16, and the like.

As a display method of the ultrasound image and the endoscope image, a method in which one image is switched to one of other images and displayed on the monitor 20 or a method in which two or more images are simultaneously arranged and displayed may be applied.

In the embodiment, although the ultrasound image and the endoscope image are displayed on one monitor 20, a monitor for ultrasound image display and a monitor for endoscope image display may be provided separately. Alternatively, the ultrasound image and the endoscope image may be displayed in a display form other than the monitor 20, for example, in a form of being displayed on a display of a terminal carried with the operator.

The console (instruction acquisition unit) 100 is an example of an instruction acquisition unit that acquires an instruction input from the operator (user), and is a device that is provided to allow the operator to input necessary information in a case of ultrasound diagnosis, to issue an instruction to start ultrasound diagnosis to the ultrasound observation device 14, and the like. The console 100 is constituted of, for example, a keyboard, a mouse, a trackball, a touch pad, a touch panel, and the like. In a case where the console 100 is operated, a CPU (control circuit) 152 (see FIG. 4) of the ultrasound observation device 14 controls respective units (for example, a reception circuit 142 and a transmission circuit 144 described below) of the device according to the operation content.

Specifically, the operator inputs examination information (for example, examination order information including date, an order number, and the like and patient information including a patient ID, a patient name, and the like) through the console 100 in a state before starting ultrasound diagnosis. After the input of the examination information is completed, in a case where the operator issues an instruction to start ultrasound diagnosis through the console 100, the CPU 152 of the ultrasound observation device 14 controls the respective units of the ultrasound observation device 14 such that ultrasound diagnosis is executed based on the input examination information.

Furthermore, the operator can set various control parameters through the console 100 in executing ultrasound diagnosis. As the control parameters, for example, a selection result of a live mode and a freeze mode, a set value of a display depth (depth), a selection result of an ultrasound image generation mode, and the like are exemplified.

Here, the "live mode" is a mode where ultrasound images (video) obtained at a predetermined frame rate are displayed successively (displayed in real time). The "freeze mode" is a mode where an image (static image) of one frame of ultrasound images (video) generated in the past is read from a cine memory 150 described below and displayed.

In the embodiment, a plurality of ultrasound image generation modes are selectable, and specifically, include brightness (B) mode, a color flow (CF) mode, and a pulse wave (PW) mode. The B mode is a mode where amplitude of an ultrasound echo is converted into brightness and a tomographic image is displayed. The CF mode is a mode where an average blood flow speed, flow fluctuation, intensity of a flow signal, flow power, and the like are mapped to various colors and displayed on a B mode image in a superimposed manner. The PW mode is a mode where a speed (for example, a speed of a blood flow) of an ultrasound echo source detected based on transmission and reception of a pulse wave is displayed.

The above-described ultrasound image generation modes are merely examples, and modes other than the above-described three kinds of modes, for example, an amplitude (A) mode, a motion (M) mode, a contrast radiography mode, and the like may be further included.

Configuration of Ultrasound Endoscope 12

Figure 2:
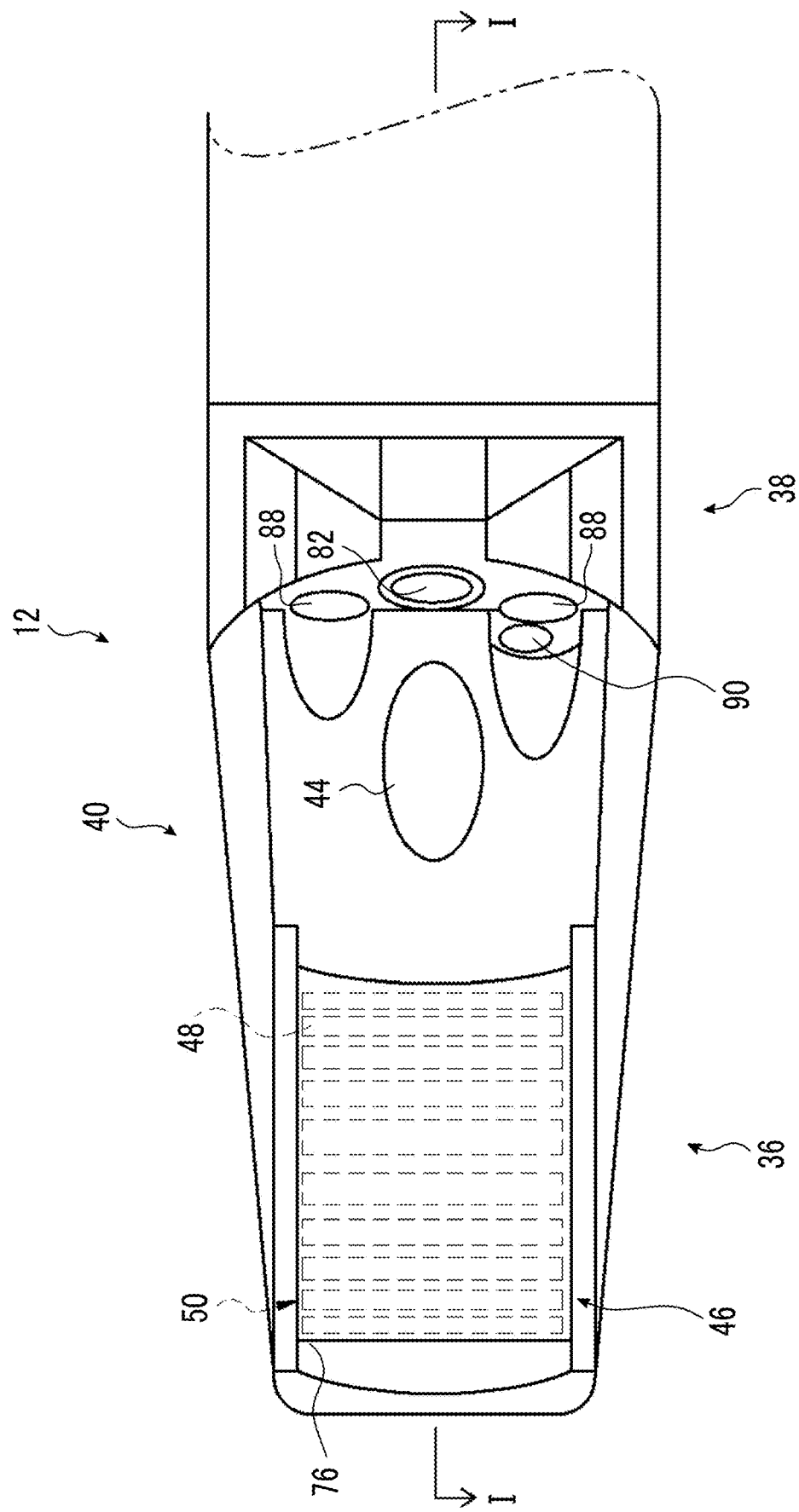
FIG. 2 is a plan view showing a distal end portion of an insertion part of an ultrasound endoscope and the periphery of the distal end portion.
Figure 3:
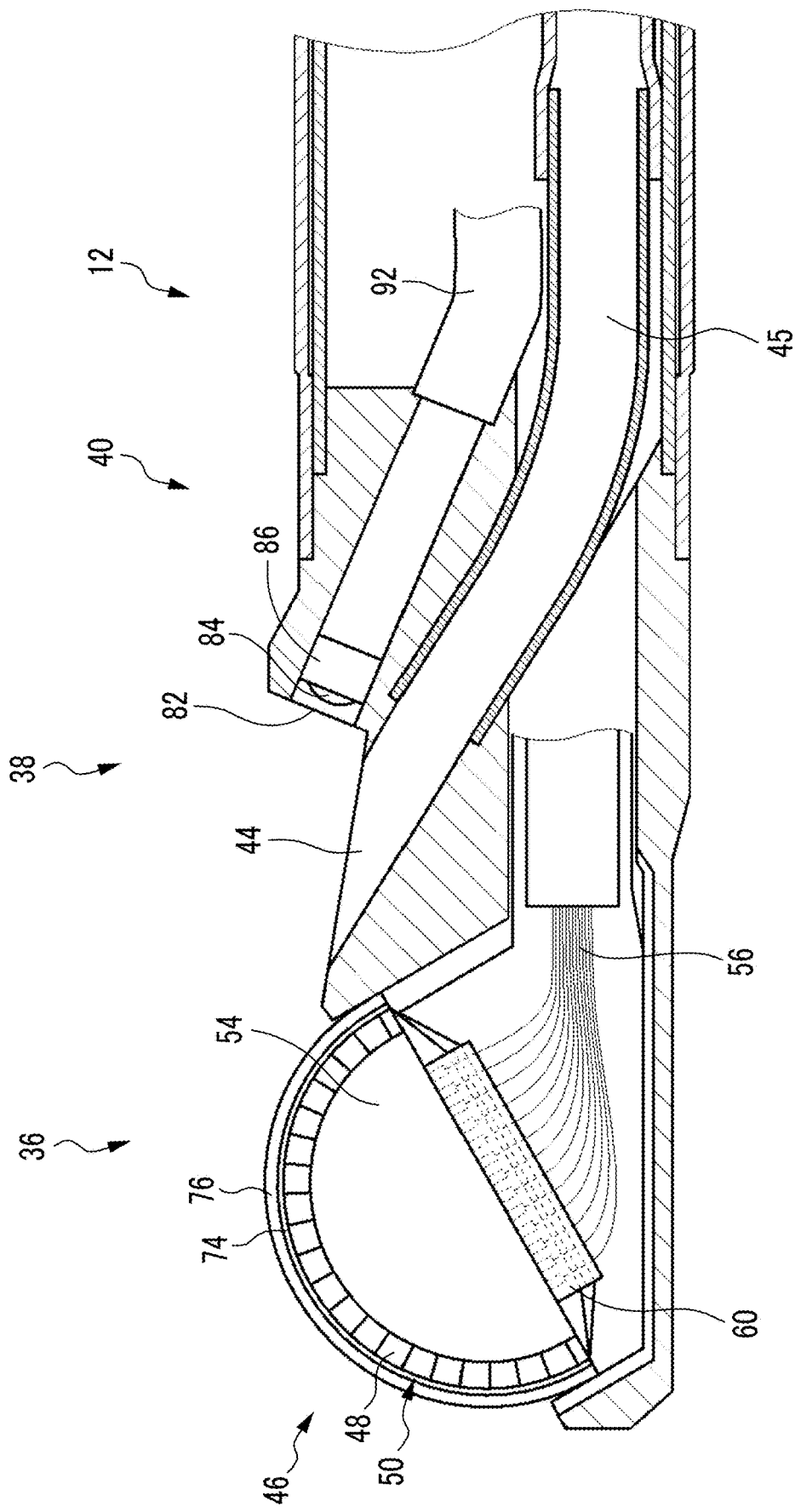
FIG. 3 is a sectional view showing a cross section of the distal end portion of the insertion part of the ultrasound endoscope taken along the line I-I of FIG. 2.
Figure 4:
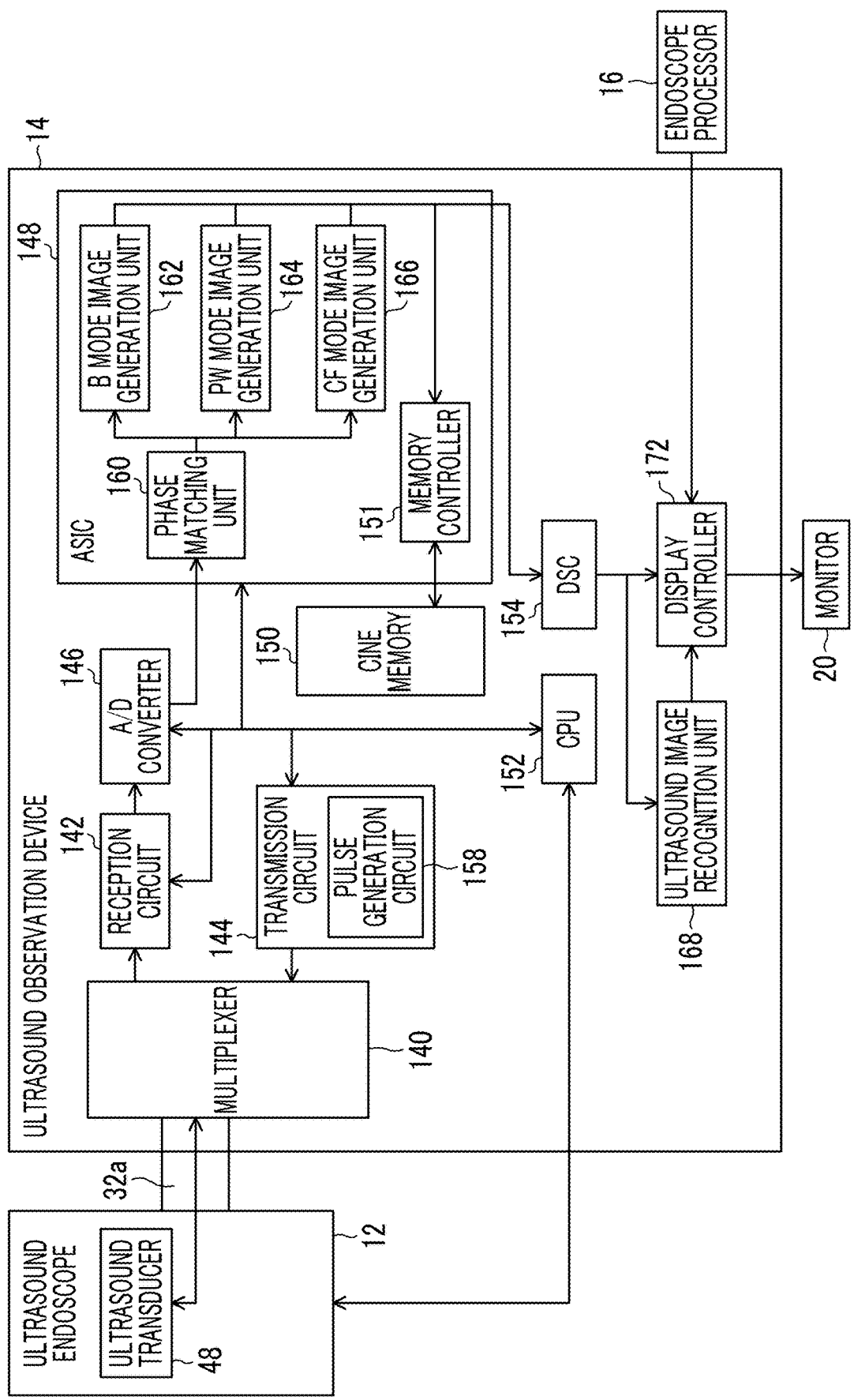
FIG. 4 is a block diagram showing the configuration of an ultrasound observation device.

Next, the configuration of the ultrasound endoscope 12 will be described referring to FIGS. 1, 2, 3, and 4. FIG. 2 is an enlarged plan view of the distal end portion 40 of the insertion part 22 of the ultrasound endoscope 12 and the periphery of the distal end portion 40. FIG. 3 is a sectional view showing a cross section of the distal end portion 40 of the insertion part 22 of the ultrasound endoscope 12 taken along the line I-I of FIG. 2. FIG. 4 is a block diagram showing the configuration of the ultrasound observation device 14.

As described above, the ultrasound endoscope 12 has the insertion part 22 and the operating part 24. As shown in FIG. 1, the insertion part 22 comprises the distal end portion 40, a bending portion 42, and a flexible portion 43 in order from the distal end side (free end side). As shown in FIG. 2, the ultrasound observation portion 36 and the endoscope observation portion 38 are provided in the distal end portion 40. As shown in FIG. 3, the ultrasound transducer unit 46 comprising a plurality of ultrasound transducers 48 is disposed in the ultrasound observation portion 36.

Furthermore, as shown in FIG. 2, a treatment tool lead-out port 44 is provided in the distal end portion 40. The treatment tool lead-out port 44 serves as an outlet of a treatment tool (not shown), such as forceps, a puncture needle, or a high-frequency scalpel. Furthermore, the treatment tool lead-out port 44 serves as a suction port in sucking aspirates, such as blood or filth inside the body.

The bending portion 42 is a portion consecutively provided on a proximal end side (a side opposite to a side on which the ultrasound transducer unit 46 is provided) than the distal end portion 40, and is freely bent. The flexible portion 43 is a portion that connects the bending portion 42 and the operating part 24, has flexibility, and is provided in an elongated and extended state.

A plurality of pipe lines for air and water supply and a plurality of pipe lines for suction are formed inside each of the insertion part 22 and the operating part 24. In addition, a treatment tool channel 45 of which one end communicates with the treatment tool lead-out port 44 is formed inside each of the insertion part 22 and the operating part 24.

Next, the ultrasound observation portion 36, the endoscope observation portion 38, the water supply tank 21a, the suction pump 21b, and the operating part 24 among the components of the ultrasound endoscope 12 will be described in detail.

Ultrasound Observation Portion 36

The ultrasound observation portion 36 is a portion that is provided to acquire an ultrasound image, and is disposed on the distal end side in the distal end portion 40 of the insertion part 22. As shown in FIG. 3, the ultrasound observation portion 36 comprises the ultrasound transducer unit 46, a plurality of coaxial cables 56, and a flexible printed circuit (FPC) 60.

The ultrasound transducer unit 46 corresponds to an ultrasound probe (probe), transmits ultrasonic waves using an ultrasound transducer array 50, in which a plurality of ultrasound transducers 48 described below are arranged, inside a body cavity of a patient, receives reflected waves (echoes) of the ultrasonic waves reflected by the observation target part, and outputs reception signals. The ultrasound transducer unit 46 according to the embodiment is a convex type, and transmits ultrasonic waves radially (in an arc shape). Note that the type (model) of the ultrasound transducer unit 46 is not particularly limited to the convex type, and other types may be used as long as ultrasonic waves can be transmitted and received. For example, a linear type, a radial type, or the like may be used.

As shown in FIG. 3, the ultrasound transducer unit 46 is constituted by laminating a backing material layer 54, the ultrasound transducer array 50, an acoustic matching layer 74, and an acoustic lens 76.

The ultrasound transducer array 50 has a plurality of ultrasound transducers 48 (ultrasound transducers) arranged in a one-dimensional array. In more detail, the ultrasound transducer array 50 is constituted by arranging N (for example, N=128) ultrasound transducers 48 at regular intervals in a convex bent shape along an axial direction of the distal end portion 40 (a longitudinal axis direction of the insertion part 22). The ultrasound transducer array 50 may be constituted by arranging a plurality of ultrasound transducers 48 in a two-dimensional array.

Each of the N ultrasound transducers 48 is constituted by disposing electrodes on both surfaces of a piezoelectric element (piezoelectric body). As the piezoelectric element, barium titanate ($BaTiO_3$), lead zirconate titanate (PZT), potassium niobate ($KNbO_3$), or the like is used.

The electrodes have an individual electrode (not shown) individually provided for each of a plurality of ultrasound transducers 48 and a transducer ground (not shown) common to a plurality of ultrasound transducers 48. The electrodes are electrically connected to the ultrasound observation device 14 through the coaxial cables 56 and the FPC 60.

A pulsed drive voltage is supplied as an input signal (transmission signal) from the ultrasound observation device 14 to each ultrasound transducer 48 through the coaxial cables 56. In a case where the drive voltage is applied to the electrodes of the ultrasound transducer 48, the piezoelectric element expands and contracts to drive (vibrate) the ultrasound transducer 48. As a result, a pulsed ultrasonic wave is output from the ultrasound transducer 48. In this case, the amplitude of the ultrasonic wave output from the ultrasound transducer 48 has magnitude according to intensity (output intensity) when the ultrasound transducer 48 outputs the ultrasonic wave. Here, the output intensity is defined as the magnitude of sound pressure of the ultrasonic wave output from the ultrasound transducer 48.

Each ultrasound transducer 48 vibrates (is driven) with reception of a reflected wave (echo) of the ultrasonic wave, and the piezoelectric element of each ultrasound transducer 48 generates an electric signal. The electric signal is output as a reception signal of the ultrasonic wave from the ultrasound transducer 48 toward the ultrasound observation device 14. In this case, the magnitude (voltage value) of the electric signal output from the ultrasound transducer 48 is magnitude according to reception sensitivity when the ultrasound transducer 48 receives the ultrasonic wave. Here, the reception sensitivity is defined as a ratio of the amplitude of the electric signal output from the ultrasound transducer 48 with reception of the ultrasonic wave to the amplitude of the ultrasonic wave transmitted from the ultrasound transducer 48.

In the embodiment, the N ultrasound transducers 48 are driven sequentially by an electronic switch, such as a multiplexer 140 (see FIG. 4), scanning with ultrasonic waves is performed in a scanning range along a curved surface on which the ultrasound transducer array 50 is disposed, for example, a range of about several tens of mm from the center of curvature of the curved surface. In more detail, in a case where a B mode image (tomographic image) is acquired as an ultrasound image, the drive voltage is supplied to m (for example, m=N/2) continuously arranged ultrasound transducers 48 (hereinafter, referred to as drive target transducers) among the N ultrasound transducers 48 by selection of opening channel selection of the multiplexer 140. With this, the m drive target transducers are driven, and an ultrasonic wave is output from each drive target transducer of the opening channel. The ultrasonic waves output from the m drive target transducers are immediately composed, and the composite wave (ultrasound beam) is transmitted toward the observation target part. Thereafter, the m drive target transducers receive ultrasonic waves (echoes) reflected by the observation target part and output electric signals (reception signals) according to reception sensitivity at that moment.

Then, the above-described series of steps (that is, the supply of the drive voltage, the transmission and reception of the ultrasonic waves, and the output of the electric signal) are repeatedly performed while shifting the positions of the drive target transducers among the N ultrasound transducers 48 one by one (one ultrasound transducer 48 at a time). Specifically, the above-described series of steps are started from m drive target transducers on both sides of the ultrasound transducer 48 positioned at one end among the N ultrasound transducers 48. Then, the above-described series of steps are repeated each time the positions of the drive target transducers are shifted due to switching of the opening channel by the multiplexer 140. Finally, the above-described series of steps are repeatedly performed N times in total up to m drive target transducers on both sides of the ultrasound transducer 48 positioned at the other end among the N ultrasound transducers 48.

The backing material layer 54 supports each ultrasound transducer 48 of the ultrasound transducer array 50 from a rear surface side. Furthermore, the backing material layer 54 has a function of attenuating ultrasonic waves propagating to the backing material layer 54 side among ultrasonic waves emitted from the ultrasound transducers 48 or ultrasonic waves (echoes) reflected by the observation target part. A backing material is a material having rigidity, such as hard rubber, and an ultrasonic wave attenuation material (ferrite, ceramics, or the like) is added as necessary.

The acoustic matching layer 74 is superimposed on the ultrasound transducer array 50, and is provided for acoustic impedance matching between the body of the patient and the ultrasound transducer 48. The acoustic matching layer 74 is provided, whereby it is possible to increase the transmittance of the ultrasonic wave. As a material of the acoustic matching layer 74, various organic materials of which a value of acoustic impedance is closer to that of the body of the patient than the piezoelectric element of the ultrasound transducer 48 can be used. As the material of the acoustic matching layer 74, specifically, epoxy-based resin, silicone rubber, polyimide, polyethylene, and the like are exemplified.

The acoustic lens 76 superimposed on the acoustic matching layer 74 converges ultrasonic waves emitted from the ultrasound transducer array 50 toward the observation target part. The acoustic lens 76 is made of, for example, silicone-based resin (millable silicone rubber (HTV rubber), liquid silicone rubber (RTV rubber), or the like), butadiene-based resin, polyurethane-based resin, or the like, and powder of titanium oxide, alumina, silica, or the like is mixed as necessary.

The FPC 60 is electrically connected to the electrodes of each ultrasound transducer 48. Each of a plurality of coaxial cables 56 is wired to the FPC 60 at one end. Then, in a case where the ultrasound endoscope 12 is connected to the ultrasound observation device 14 through the ultrasound connector 32a, each of a plurality of coaxial cables 56 is electrically connected to the ultrasound observation device 14 at the other end (a side opposite to the FPC 60 side).

Endoscope Observation Portion 38

The endoscope observation portion 38 is a portion that is provided to acquire an endoscope image, and is disposed on a proximal end side than the ultrasound observation portion 36 in the distal end portion 40 of the insertion part 22. As shown in FIGS. 2 and 3, the endoscope observation portion 38 is constituted of the observation window 82, the objective lens 84, the solid-state imaging element 86, the illumination windows 88, a cleaning nozzle 90, a wiring cable 92, and the like.

The observation window 82 is attached in a state inclined with respect to the axial direction (the longitudinal axis direction of the insertion part 22) in the distal end portion 40 of the insertion part 22. Light reflected by the observation target adjacent part and incident from the observation window 82 is formed on an imaging surface of the solid-state imaging element 86 by the objective lens 84.

The solid-state imaging element 86 photoelectrically converts reflected light of the observation target adjacent part transmitted through the observation window 82 and the objective lens 84 and formed on the imaging surface, and outputs an imaging signal. As the solid-state imaging element 86, a charge coupled device (CCD), a complementary metal oxide semiconductor (CMOS), or the like can be used. A captured image signal output from the solid-state imaging element 86 is transmitted to the endoscope processor 16 by the universal cord 26 by way of the wiring cable 92 extending from the insertion part 22 to the operating part 24.

The illumination windows 88 are provided at both side positions of the observation window 82. An exit end of the light guide (not shown) is connected to the illumination windows 88. The light guide extends from the insertion part 22 to the operating part 24, and an incidence end of the light guide is connected to the light source device 18 connected through the universal cord 26. Illumination light emitted from the light source device 18 is transmitted through the light guide, and the observation target adjacent part is irradiated with illumination light from the illumination windows 88.

The cleaning nozzle 90 is an ejection hole formed in the distal end portion 40 of the insertion part 22 in order to clean the surfaces of the observation window 82 and the illumination windows 88, and air or a cleaning liquid is ejected from the cleaning nozzle 90 toward the observation window 82 and the illumination windows 88. In the embodiment, the cleaning liquid ejected from the cleaning nozzle 90 is water, in particular, degassed water. Note that the cleaning liquid is not particularly limited, and other liquids, for example, normal water (water that is not degassed) may be used.

Water Supply Tank 21a and Suction Pump 21b

The water supply tank 21a is a tank that stores degassed water, and is connected to the light source connector 32c by an air and water supply tube 34a. Degassed water is used as the cleaning liquid that is ejected from the cleaning nozzle 90.

The suction pump 21b sucks aspirates (including degassed water supplied for cleaning) into the body cavity through the treatment tool lead-out port 44. The suction pump 21b is connected to the light source connector 32c by a suction tube 34b. The ultrasound endoscope system 10 may comprise an air supply pump that supplies air to a predetermined air supply destination, or the like.

Inside the insertion part 22 and the operating part 24, the treatment tool channel 45 and an air and water supply pipe line (not shown) are provided.

The treatment tool channel 45 communicates a treatment tool insertion port 30 and the treatment tool lead-out port 44 provided in the operating part 24. Furthermore, the treatment tool channel 45 is connected to a suction button 28b provided in the operating part 24. The suction button 28b is connected to the suction pump 21b in addition to the treatment tool channel 45.

The air and water supply pipe line communicates with the cleaning nozzle 90 on one end side, and is connected to an air and water supply button 28a provided in the operating part 24 on the other end side. The air and water supply button 28a is connected to the water supply tank 21a in addition to the air and water supply pipe line.

Operating Part 24

The operating part 24 is a portion that is operated by the operator at the time of a start of ultrasound diagnosis, during diagnosis, at the time of an end of diagnosis, and the like, and has one end to which one end of the universal cord 26 is connected. Furthermore, as shown in FIG. 1, the operating part 24 has the air and water supply button 28a, the suction button 28b, a pair of angle knobs 29, and a treatment tool insertion port (forceps port) 30.

In a case where each of a pair of angle knobs 29 is moved rotationally, the bending portion 42 is remotely operated to be bent and deformed. With the deformation operation, it is possible to direct the distal end portion 40 of the insertion part 22, in which the ultrasound observation portion 36 and the endoscope observation portion 38 are provided, to a desired direction.

The treatment tool insertion port 30 is a hole formed in order that the treatment tool (not shown), such as forceps, is inserted thereinto, and communicates with the treatment tool lead-out port 44 through the treatment tool channel 45. The treatment tool inserted into the treatment tool insertion port 30 is introduced from the treatment tool lead-out port 44 into the body cavity after passing through the treatment tool channel 45.

The air and water supply button 28a and the suction button 28b are two-stage switching type push buttons, and are operated in order to switch opening and closing of the pipe line provided inside each of the insertion part 22 and the operating part 24.

Schematic Configuration of Endoscope Processor 16

Here, although the detailed configuration of the endoscope processor 16 will not be repeated, the endoscope processor 16 comprises general components known in the related art for capturing an endoscope image. An endoscope image generated by the endoscope processor 16 is transferred to a display controller 172 of the ultrasound observation device 14 described below.

Configuration of Ultrasound Observation Device 14

The ultrasound observation device 14 makes the ultrasound transducer unit 46 transmit and receive ultrasonic waves and generates an ultrasound image by imaging reception signals output from the ultrasound transducers 48 (in detail, the drive target transducers) at the time of reception of the ultrasonic waves. Furthermore, the ultrasound observation device 14 displays the endoscope image transferred from the endoscope processor 16, and the like on the monitor 20 in addition to the generated ultrasound image.

As shown in FIG. 4, the ultrasound observation device 14 has the multiplexer 140, the reception circuit 142, the transmission circuit 144, an A/D converter 146, an application specific integrated circuit (ASIC) 148, the cine memory 150, a central processing unit (CPU) 152, a digital scan converter (DSC) 154, an ultrasound image recognition unit 168, and the display controller 172.

The reception circuit 142 and the transmission circuit 144 are electrically connected to the ultrasound transducer array 50 of the ultrasound endoscope 12. The multiplexer 140 selects a maximum of m drive target transducers from among the N ultrasound transducers 48 and opens the channels.

The transmission circuit 144 has a field programmable gate array (FPGA), a pulser (pulse generation circuit 158), a switch (SW), and the like, and is connected to the multiplexer 140 (MUX). An application-specific integrated circuit (ASIC), instead of the FPGA, may be used.

The transmission circuit 144 is a circuit that supplies a drive voltage for ultrasonic wave transmission to the drive target transducers selected by the multiplexer 140 in response to a control signal sent from the CPU 152 for transmission of ultrasonic waves from the ultrasound transducer unit 46. The drive voltage is a pulsed voltage signal (transmission signal), and is applied to the electrodes of the drive target transducers through the universal cord 26 and the coaxial cables 56.

The transmission circuit 144 has a pulse generation circuit 158 that generates a transmission signal based on a control signal. Under the control of the CPU 152, the transmission circuit 144 generates a transmission signal for driving a plurality of ultrasound transducers 48 to generate ultrasonic waves using the pulse generation circuit 158 and supplies the transmission signal to a plurality of ultrasound transducers 48. In more detail, under the control of the CPU 152, in a case of performing ultrasound diagnosis, the transmission circuit 144 generates a transmission signal having a drive voltage for performing ultrasound diagnosis using the pulse generation circuit 158.

The reception circuit 142 is a circuit that receives electric signals output from the drive target transducers, which receive the ultrasonic waves (echoes), that is, reception signals. Furthermore, the reception circuit 142 amplifies reception signals received from the ultrasound transducers 48 in response to a control signal sent from the CPU 152 and delivers the signals after amplification to the A/D converter 146. The A/D converter 146 is connected to the reception circuit 142, converts the reception signals received from the reception circuit 142 from analog signals to digital signals and outputs the digital signals after conversion to the ASIC 148.

The ASIC 148 is connected to the A/D converter 146. As shown in FIG. 4, the ASIC 148 is constituted of a phase matching unit 160, a B mode image generation unit 162, a PW mode image generation unit 164, a CF mode image generation unit 166, and a memory controller 151.

In the embodiment, although the above-described functions (specifically, the phase matching unit 160, the B mode image generation unit 162, the PW mode image generation unit 164, the CF mode image generation unit 166, and the memory controller 151) are realized by a hardware circuit, such as the ASIC 148, the invention is not limited thereto. The above-described functions may be realized by making a central processing unit (CPU) and software (computer program) for executing various kinds of data processing cooperate with each other.

The phase matching unit 160 executes processing of giving a delay time to the reception signals (reception data) digitized by the A/D converter 146 and performing phasing addition (performing addition after matching the phases of the reception data). With the phasing addition processing, sound ray signals in which the focus of the ultrasound echo is narrowed are generated.

The B mode image generation unit 162, the PW mode image generation unit 164, and the CF mode image generation unit 166 generate an ultrasound image based on the electric signals (strictly, sound ray signals generated by phasing addition on the reception data) output from the drive target transducers among a plurality of ultrasound transducers 48 when the ultrasound transducer unit 46 receives the ultrasonic waves.

The B mode image generation unit 162 is an image generation unit that generates a B mode image as a tomographic image of the inside (the inside of the body cavity) of the patient. The B mode image generation unit 162 performs correction of attenuation due to a propagation distance on each of the sequentially generated sound ray signals according to a depth of a reflection position of the ultrasound wave through sensitivity time gain control (STC). Furthermore, the B mode image generation unit 162 executes envelope detection processing and logarithm (Log) compression processing on the sound ray signal after correction to generate a B mode image (image signal).

The PW mode image generation unit 164 is an image generation unit that generates an image indicating a speed of a blood flow in a predetermined direction. The PW mode image generation unit 164 extracts a frequency component by performs fast Fourier transform on a plurality of sound ray signals in the same direction among the sound ray signals sequentially generated by the phase matching unit 160. Thereafter, the PW mode image generation unit 164 calculates the speed of the blood flow from the extracted frequency component and generates a PW mode image (image signal) indicating the calculated speed of the blood flow.

The CF mode image generation unit 166 is an image generation unit that generates an image indicating information regarding a blood flow in a predetermined direction. The CF mode image generation unit 166 generates an image signal indicating information regarding the blood flow by obtaining autocorrelation of a plurality of sound ray signals in the same direction among the sound ray signals sequentially generated by the phase matching unit 160. Thereafter, the CF mode image generation unit 166 generates a CF mode image (image signal) as a color image, in which information relating to the blood flow is superimposed on the B mode image generated by the B mode image generation unit 162, based on the above-described image signal.

The memory controller 151 stores the image signal generated by the B mode image generation unit 162, the PW mode image generation unit 164 or the CF mode image generation unit 166 in the cine memory 150.

The DSC 154 is connected to the ASIC 148, converts (raster conversion) the signal of the image generated by the B mode image generation unit 162, the PW mode image generation unit 164, or the CF mode image generation unit 166 into an image signal compliant with a normal television signal scanning system, executes various kinds of necessary image processing, such as gradation processing, on the image signal, and then, outputs the image signal to the ultrasound image recognition unit 168 and the display controller 172.

Here, in the ultrasound endoscope system 10 shown in FIG. 1, a part that acquires an endoscope image and an ultrasound image generated by the ultrasound endoscope 12, the ultrasound observation device 14, and the endoscope processor 16 constitutes an image acquisition unit of the invention.

The image acquisition unit acquires a medical image (endoscope image and ultrasound image) of an observation target part inside the body of the subject in each of a plurality of observation steps in which an observation order of the observation target part is determined.

In each of a plurality of observation steps in which the observation order of the observation target part is determined, the ultrasound image recognition unit 168 learns a relationship between an ultrasound image and a prediction step corresponding to the ultrasound image on a plurality of ultrasound images such that the prediction step corresponding to the ultrasound image (medical image) becomes close to a ground truth step of the ultrasound image, and based on a learning result, recognizes the ultrasound image subjected to raster conversion by the DSC 154, that is, outputs a prediction step predicting an observation step corresponding to the ultrasound image from the ultrasound image of the observation target part inside the body of the patient acquired by the image acquisition unit. The prediction step output from the ultrasound image recognition unit 168 is output to the display controller 172 (see FIG. 4) described below.

The observation order of the observation target part is the order of the observation target part where an ultrasound image is captured (observed) inside the body cavity of the patient. The observation order of the observation target part is determined such that a plurality of observation target parts including an intended organ or the like can be comprehensively sequentially observed primarily at the time of screening for finding out a lesion part or the like based on a position of an organ or the like inside the body in ultrasound diagnosis. An example of the observation order of the observation target part will be described below.

In a case of capturing (observing) of an ultrasound image of an observation target part inside the body of the patient according to the observation order of the observation target part, the observation step represents an order set based on the observation order of the observation target part. For example, an order of an observation step 1 corresponding to a first observation target part 1 is first, an order of an observation step 2 corresponding to a second observation target part 2 is second, an order of an observation step 3 corresponding to a third observation target part 3 is third, . . . . That is, the order of the observation step can be set so as to be the same as, for example, the observation order of the observation target part.

Furthermore, the observation step may be a partial imaging period (section or time period) set based on the observation order of the observation target part in an entire imaging period during which the ultrasound image of the observation target part inside the body of the patient is captured according to the observation order of the observation target part. For example, an imaging period of the first observation step 1 is a period during which an ultrasound image 1 is captured in the first observation target part 1, an imaging period of the second observation step 2 is a period during which an ultrasound image 2 is captured in the second observation target part 2, an imaging period of the third observation step 3 is a period during which an ultrasound image 3 is captured in the third observation target part 3, . . . . That is, an imaging period of an observation step can be set so as to be the same as, for example, a period during which an ultrasound image is captured in an observation target part corresponding to the observation step.

A prediction step is an observation step predicted by the ultrasound image recognition unit 168 from the ultrasound image acquired by the image acquisition unit based on the above-described learning result. For example, in a case where the ultrasound image acquired by the image acquisition unit is predicted to be the ultrasound image 1 captured in the first observation step 1, the prediction step is the observation step 1, in a case where the ultrasound image acquired by the image acquisition unit is predicted to be the ultrasound image 2 captured in the second observation step 2, the prediction step is the observation step 2, in a case where the ultrasound image acquired by the image acquisition unit is predicted to be the ultrasound image 3 captured in the third observation step 3, the prediction step is the observation step 3, . . . .

In each observation step, a ground truth step represents an observation step that is a ground truth corresponding to the ultrasound image acquired by the image acquisition unit. For example, a ground truth step 1 corresponding to the ultrasound image 1 captured in the first observation step 1 is the first observation step 1, a ground truth step 2 corresponding to the ultrasound image 2 captured in the second observation step 2 is the second observation step 2, a ground truth step 3 corresponding to the ultrasound image 3 captured in the third observation step 3 is the third observation step 3, . . . . That is, in each observation step, the ground truth step can be set so as to be the same as, for example, the observation step.

The observation step, the prediction step, and the ground truth step can be represented by, for example, label numbers. Furthermore, the label number can be set based on the observation order of the observation target part. For example, the label number of the observation step 1 corresponding to the first observation target part 1 can be set to '0', the label number of the observation step 2 corresponding to the second observation target part 2 can be set to '1', the label number of the observation step 3 corresponding to the third observation target part 3 can be set to '2', . . . . That is, the label number can be set so as to be the same as, for example, the observation order of the observation target part.

The label number is not particularly limited as long as the association between the prediction step and the ground truth step is known, and it is not essential to set the label number based on the observation order of the observation target part.

Figure 5:
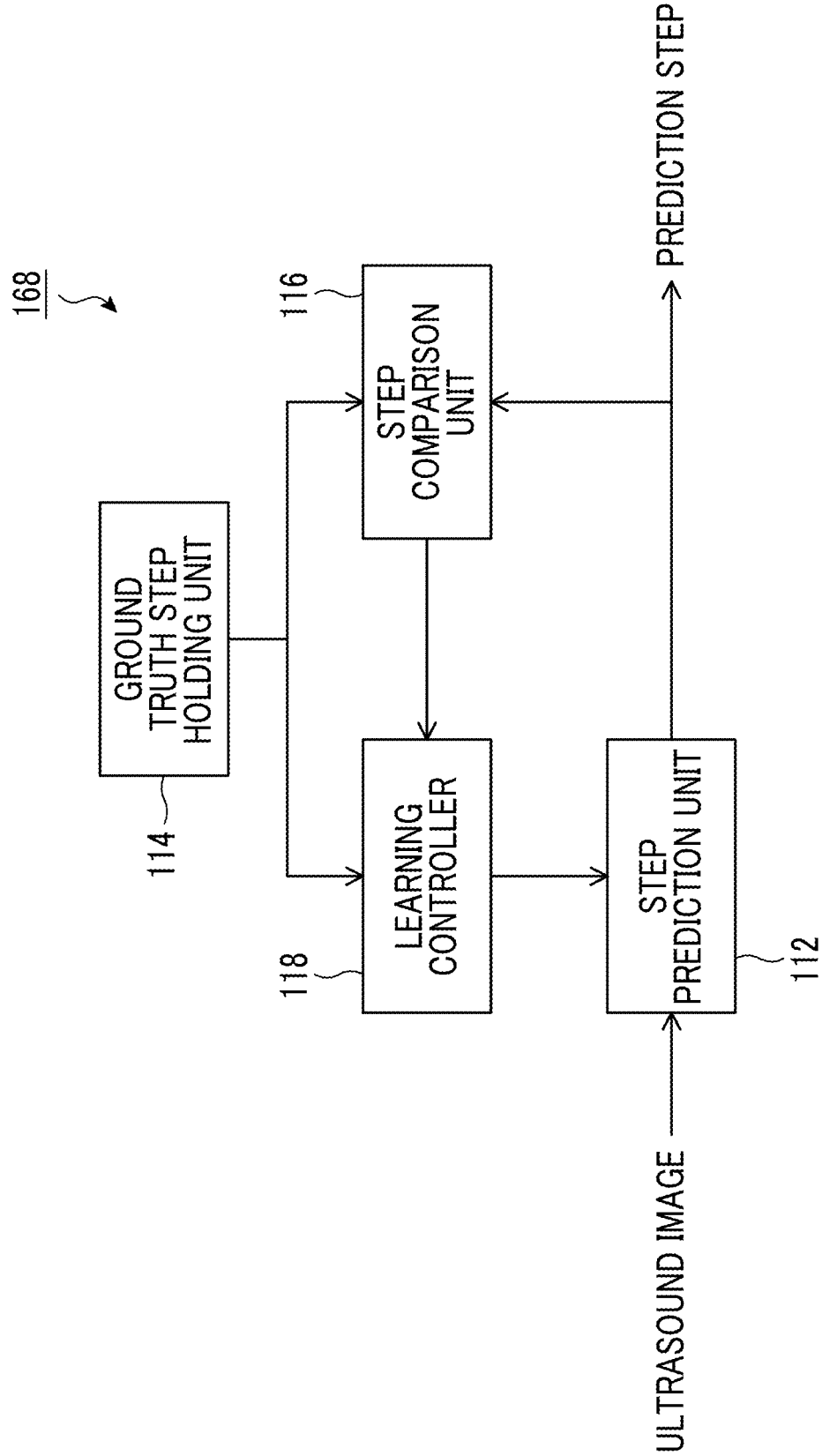
FIG. 5 is a block diagram of an embodiment representing the configuration of an ultrasound image recognition unit.

As shown in FIG. 5, the ultrasound image recognition unit 168 comprises a step prediction unit 112, a ground truth step holding unit 114, a step comparison unit 116, and a learning controller 118. The ultrasound image recognition unit 168 and the above-described image acquisition unit constitute a learning device of the invention.

In each observation step, the step prediction unit 112 outputs a prediction step predicting an observation step corresponding to an ultrasound image from the ultrasound image acquired by the image acquisition unit based on a learning result of a relationship between an ultrasound image and a prediction step corresponding to the ultrasound image. The prediction step output from the step prediction unit 112 is input to the step comparison unit 116 and the display controller 172.

The step prediction unit 112 is a learned model that learns the relationship between the ultrasound image and the prediction step corresponding to the ultrasound image using a data set having a plurality of ultrasound images obtained by imaging different observation target parts of the patient on a plurality of ultrasound images (ultrasound images for learning) by a learning method of the invention and outputs a prediction step predicting an observation step corresponding to the ultrasound image acquired by the image acquisition unit from the ultrasound image (ultrasound image for diagnosis) acquired by the image acquisition unit based on a learning result. The learned model is updated at any time and optimized by learning the relationship between the ultrasound image and the prediction step corresponding to the ultrasound image using the ultrasound image acquired by the image acquisition unit.

The step prediction unit 112 can predict the prediction step corresponding to the ultrasound image by receiving a static image or video (an ultrasound image of one frame or ultrasound images of a plurality of frames) as the ultrasound image.

The ground truth step holding unit 114 holds each ground truth step corresponding to each observation step. The ground truth steps held in the ground truth step holding unit 114 are input to the step comparison unit 116 and the learning controller 118.

For example, the ground truth steps corresponding to the observation steps 1, 2, 3, . . . are observation steps 1, 2, 3, . . . . That is, the ground truth step corresponding to each observation step is the same as each observation step. Accordingly, for example, the ground truth step holding unit 114 holds the observation steps 1, 2, 3, . . . as the ground truth steps 1, 2, 3, . . . corresponding to the observation steps 1, 2, 3, . . . .

In each observation step, the step comparison unit 116 compares the prediction step output from the step prediction unit 112 with the ground truth step corresponding to the prediction step among the ground truth steps held in the ground truth step holding unit 114.

As a result of comparison by the step comparison unit 116, a result about whether or not the prediction step and the ground truth step coincide with each other, how much the difference between the prediction step and the ground truth step is in a case where the prediction step and the ground truth step do not coincide with each other, or the like is output from the step comparison unit 116. The result of comparison output from the step comparison unit 116 is input to the learning controller 118.

In each observation step, the learning controller 118 makes the step prediction unit 112 learn the relationship between the ultrasound image and the prediction step based on the result of comparison by the step comparison unit 116 such that the prediction step becomes close to the ground truth step. A control signal for making the step prediction unit 112 learn the relationship between the ultrasound image and the prediction step is output from the learning controller 118. The control signal is input to the step prediction unit 112.

A learning method is not particularly limited as long as it is possible to learn the relationship between the ultrasound image and the prediction step on a plurality of ultrasound images, and to generate a learned model.

As the learning method, for example, deep learning or the like that uses a hierarchical structure type neural network as an example of machine learning, which is one of artificial intelligence (AI) techniques, can be used.

Machine learning other than deep learning may be used, an artificial intelligence technique other than machine learning may be used, or a learning method other than an artificial intelligence technique may be used.

For example, the step prediction unit 112 can be constituted of a convolutional neural network (NN Network) using uses a loss function. In this case, in a case where the observation step, the prediction step, and the ground truth step are represented by the label numbers, the learning controller 118 makes the convolutional neural network learn the relationship between the ultrasound image and the prediction step such that an output of the loss function calculated based on a difference between the label number of the prediction step and the label number of the ground truth step is minimized.

An observation order of an observation target part in a case of capturing an ultrasound image inside the body of the patient and a representative observation step are roughly determined. For this reason, in each observation step, the learning controller 118 can make the step prediction unit 112 learn the ultrasound image of the observation target part of the patient acquired by the image acquisition unit and a prediction step predicting an observation step corresponding to the ultrasound image in association with each other.

Hereinafter, a representative observation step in a case of capturing the ultrasound image of the observation target part inside the body of the patient according to the observation order will be described.

As the representative observation step, for example, there are observation steps 1 to 12 shown in Table 1 described below.

TABLE 1

| Observation Step | Label Number | Observation Target Part |
| --- | --- | --- |
| Step 1 | 0 | hepatic left lobe |
| Step 2 | 1 | confluence of aorta, celiac trunk, and superior mesenteric artery |
| Step 3 | 2 | pancreatic body |
| Step 4 | 3 | pancreatic tail |
| Step 5 | 4 | confluence of splenic vein, superior mesenteric vein, and portal vein |
| Step 6 | 5 | pancreatic head |
| Step 7 | 6 | gallbladder |
| Step 8 | 7 | portal vein |
| Step 9 | 8 | common bile duct |
| Step 10 | 9 | gallbladder |
| Step 11 | 10 | pancreatic uncinate process |
| Step 12 | 11 | papilla |

In Table 1, the observation steps 1 to 12 are represented by label numbers 0 to 11.

A hepatic left lobe of an observation step 1 represented by a label number 0, a confluence of an aorta, a celiac trunk, and a superior mesenteric artery of an observation step 2 represented by a label number 1, a pancreatic body of an observation step 3 represented by a label number 2, a pancreatic tail of an observation step 4 represented by a label number 3, a confluence of a splenic vein, a superior mesenteric vein, and a portal vein of an observation step 5 represented by a label number 4, a pancreatic head of an observation step 6 represented by a label number 5, and a gallbladder of an observation step 7 represented by a label number 6 are representative observation points from the inside of a stomach. Furthermore, a portal vein of an observation step 8 represented by a label number 7, a common bile duct of an observation step 9 represented by a label number 8, and a gallbladder of an observation step 10 represented by a label number 9 are representative observation points from a duodenal bulb, and a pancreatic uncinate process of an observation step 11 represented by a label number 10, and a papilla of an observation step 12 represented by a label number 11 are representative observation points from a pars descendens duodeni.

The observation order of the observation target part is an example, and the observation order of the observation target part may be slightly different depending on the operator. For this reason, a plurality of lists of the observation order of the observation target part may be prepared according to the operators, and the list to be used, that is, the observation order of the observation target part may be switched depending on the operator. Alternatively, the operator may register a desired list.

In the ultrasound image recognition unit 168, in each observation step, the prediction step predicting the observation step corresponding to the ultrasound image from the ultrasound image acquired by the image acquisition unit is output based on the learning result by the step prediction unit 112.

Subsequently, in each observation step, the prediction step is compared with a ground truth step corresponding to the prediction step by the step comparison unit 116.

Subsequently, in each observation step, the learning controller 118 makes the step prediction unit 112 learn the relationship between the ultrasound image and the prediction step based on the result of comparison by the step comparison unit 116 such that the prediction step becomes close to the ground truth step.

Hereinafter, similarly, each time the ultrasound image is acquired by the image acquisition unit, the above-described operation is repeatedly performed.

Subsequently, the display controller 172 makes the monitor 20 display the endoscope image and the ultrasound image. Furthermore, the display controller 172 makes the monitor 20 display information relating to the prediction step recognized by the ultrasound image recognition unit 168.

The display controller 172 can make the monitor 20 display, as information relating to the prediction step, for example, the prediction step (prediction step 1, 2, 3, . . . ), the label number of the prediction step, and the name of the observation target part corresponding to the label number, and the like.

The cine memory 150 has a capacity for accumulating an image signal for one frame or image signals for several frames. An image signal generated by the ASIC 148 is output to the DSC 154, and is stored in the cine memory 150 by the memory controller 151. In a freeze mode, the memory controller 151 reads out the image signal stored in the cine memory 150 and outputs the image signal to the DSC 154. With this, an ultrasound image (static image) based on the image signal read from the cine memory 150 is displayed on the monitor 20.

The CPU 152 functions as a controller that controls the respective units of the ultrasound observation device 14. The CPU 152 is connected to the reception circuit 142, the transmission circuit 144, the A/D converter 146, the ASIC 148, and the like, and controls the equipment. Specifically, the CPU 152 is connected to the console 100, and controls the respective units of the ultrasound observation device 14 in compliance with examination information, control parameters, and the like input through the console 100.

In a case where the ultrasound endoscope 12 is connected to the ultrasound observation device 14 through the ultrasound connector 32a, the CPU 152 automatically recognizes the ultrasound endoscope 12 by a plug and play (PnP) system or the like.

Operation Example of Ultrasound Endoscope System 10

Figure 6:
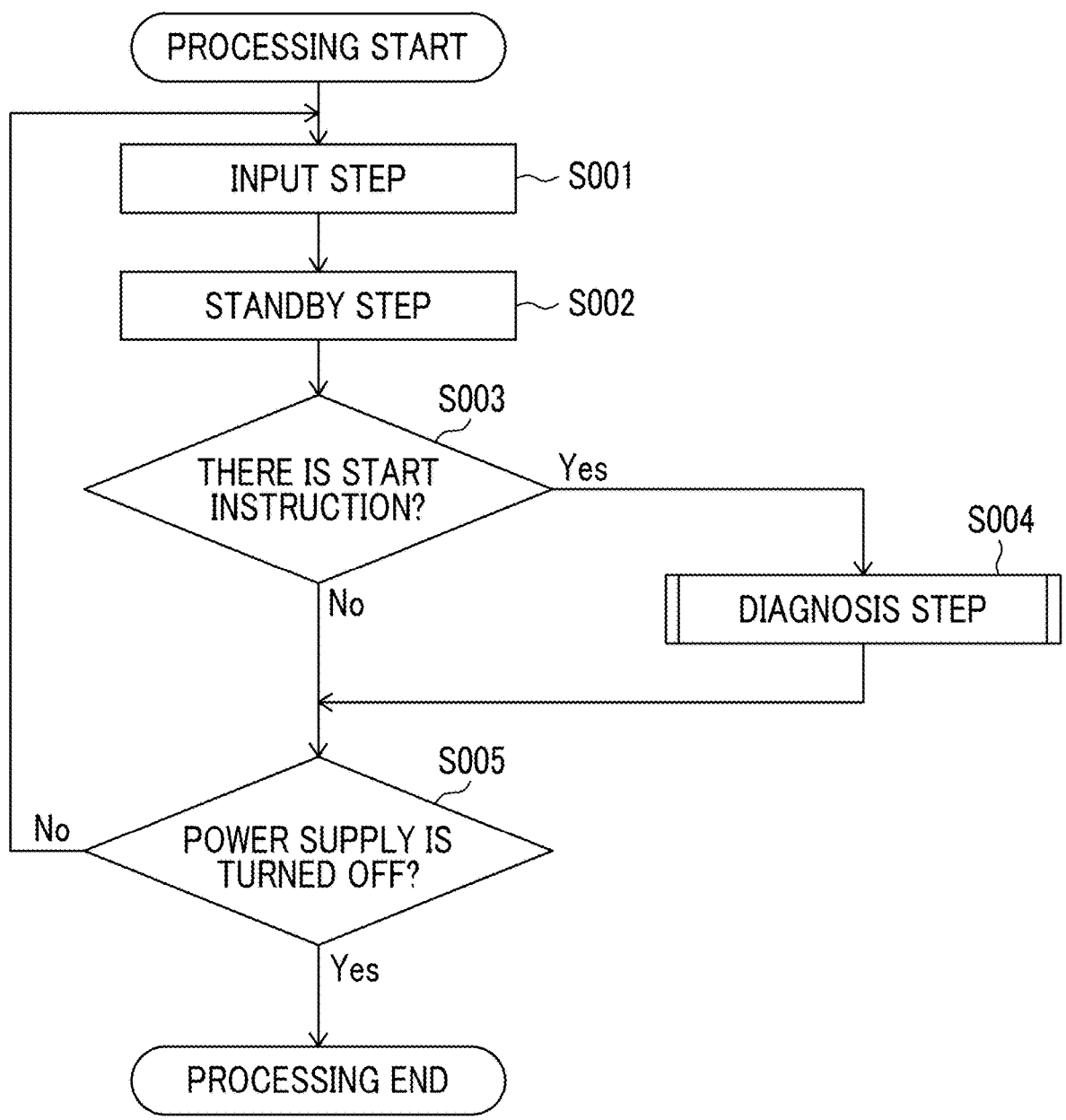
FIG. 6 is a flowchart showing a flow of diagnosis processing using the ultrasound endoscope system.
Figure 7:
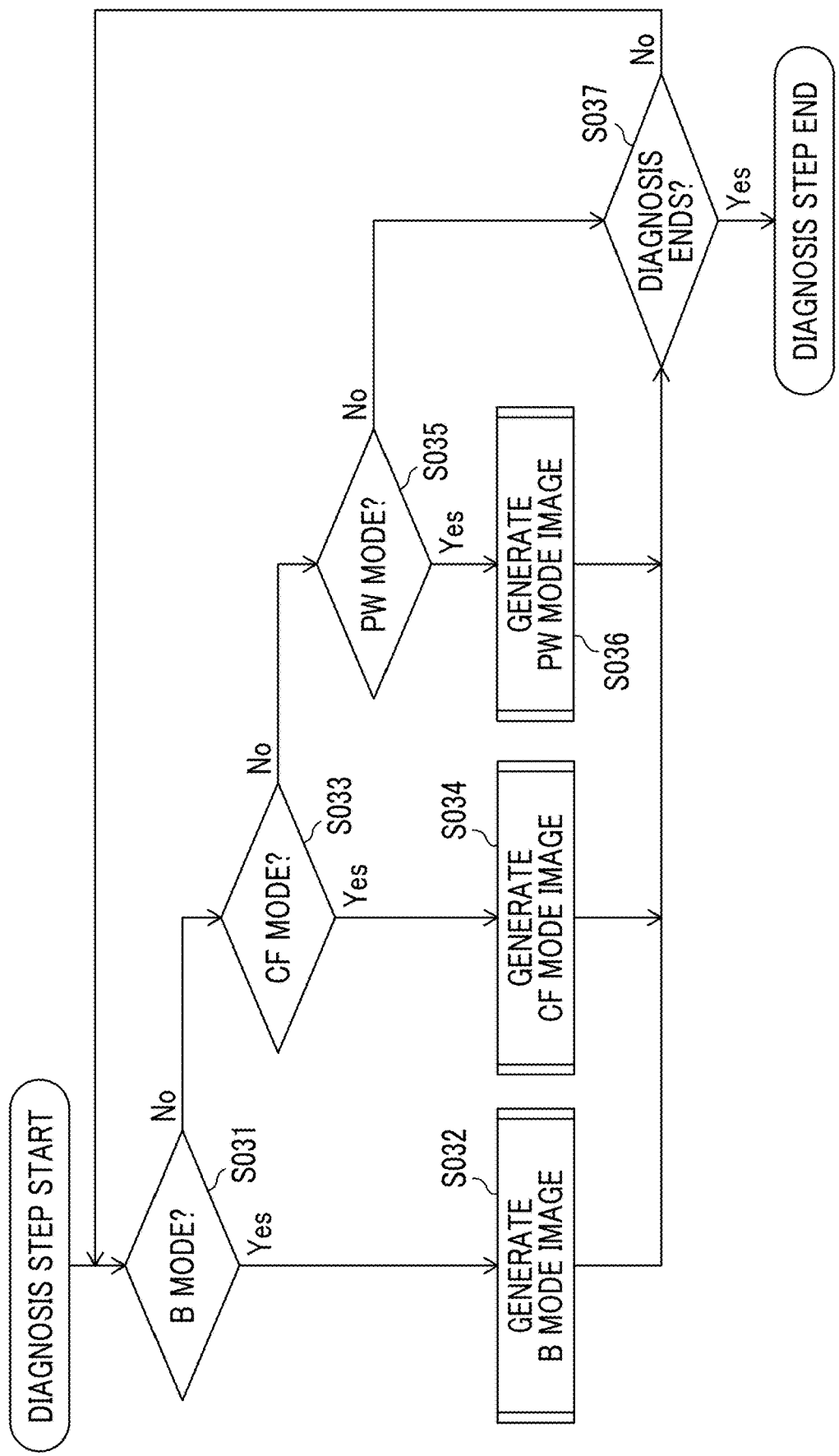
FIG. 7 is a flowchart showing a procedure of a diagnosis step during the diagnosis processing.

Next, as an operation example of the ultrasound endoscope system 10, a flow of a series of processing (hereinafter, also referred to as diagnosis processing) relating to ultrasound diagnosis will be described referring to FIGS. 6 and 7. FIG. 6 is a flowchart showing a flow of diagnosis processing using the ultrasound endoscope system 10. FIG. 7 is a flowchart showing a procedure of a diagnosis step during the diagnosis processing.

In a case where power is supplied to the respective units of the ultrasound endoscope system 10 in a state in which the ultrasound endoscope 12 is connected to the ultrasound observation device 14, the endoscope processor 16, and the light source device 18, the diagnosis processing is started with the power supply as a trigger. In the diagnosis processing, as shown in FIG. 6, first, an input step is performed (S001). In the input step, the operator inputs the examination information, the control parameters, and the like through the console 100. In a case where the input step is completed, a standby step is performed until there is an instruction to start diagnosis (S002).

Subsequently, in a case where there is a diagnosis start instruction from the operator (in S003, Yes), the CPU 152 performs control on the respective units of the ultrasound observation device 14 to perform the diagnosis step (S004). The diagnosis step progresses along the flow shown in FIG. 7, and in a case where a designated image generation mode is a B mode (in S031, Yes), control is performed on the respective units of the ultrasound observation device 14 to generate a B mode image (S032). Furthermore, in a case where the designated image generation mode is not the B mode (in S031, No) but is a CF mode (in S033, Yes), control is performed on the respective units of the ultrasound observation device 14 to generate a CF mode image (S034). In addition, in a case where the designated image generation mode is not the CF mode (in S033, No) but is a PW mode (in S035, Yes), control is performed on the respective units of the ultrasound observation device 14 to generate a PW mode image (S036). In a case where the designated image generation mode is not the PW mode (in S035, No), the process progresses to Step S037.

Subsequently, the CPU 152 determines whether or not the ultrasound diagnosis ends (S037). In a case where the ultrasound diagnosis does not end (in S037, No), the process returns to the diagnosis step S031, and the generation of the ultrasound image in each image generation mode is repeatedly performed until a diagnosis end condition is established. As the diagnosis end condition, for example, a condition that the operator gives an instruction to end diagnosis through the console 100, or the like is exemplified.

On the other hand, in a case where diagnosis end condition is established and the ultrasound diagnosis ends (in S037, Yes), the diagnosis step ends.

Subsequently, returning to FIG. 6, in a case where the respective units of the ultrasound endoscope system 10 are powered-off (in S005, Yes), the diagnosis processing ends. On the other hand, in a case where the respective units of the ultrasound endoscope system 10 are maintained in a powered-on state (in S005, No), the process returns to the input step S001, and the respective steps of the diagnosis processing described above are repeated.

Operation Example of Learning Device of the Invention

Next, an operation example of the learning device of the invention, that is, the image acquisition unit and the ultrasound image recognition unit 168 will be described.

In the ultrasound endoscope system 10, since the position of the distal end portion 40 of the insertion part 22 of the ultrasound endoscope 12 and the scanning direction of the ultrasonic waves cannot be viewed, determination regarding which part inside the body of the patient is observed at this moment is performed from an ultrasound image. Accordingly, in each observation step, the operator operates the ultrasound endoscope 12 such that a representative ultrasound image of the observation step is captured, and observes an intended observation target part.

Figure 8:
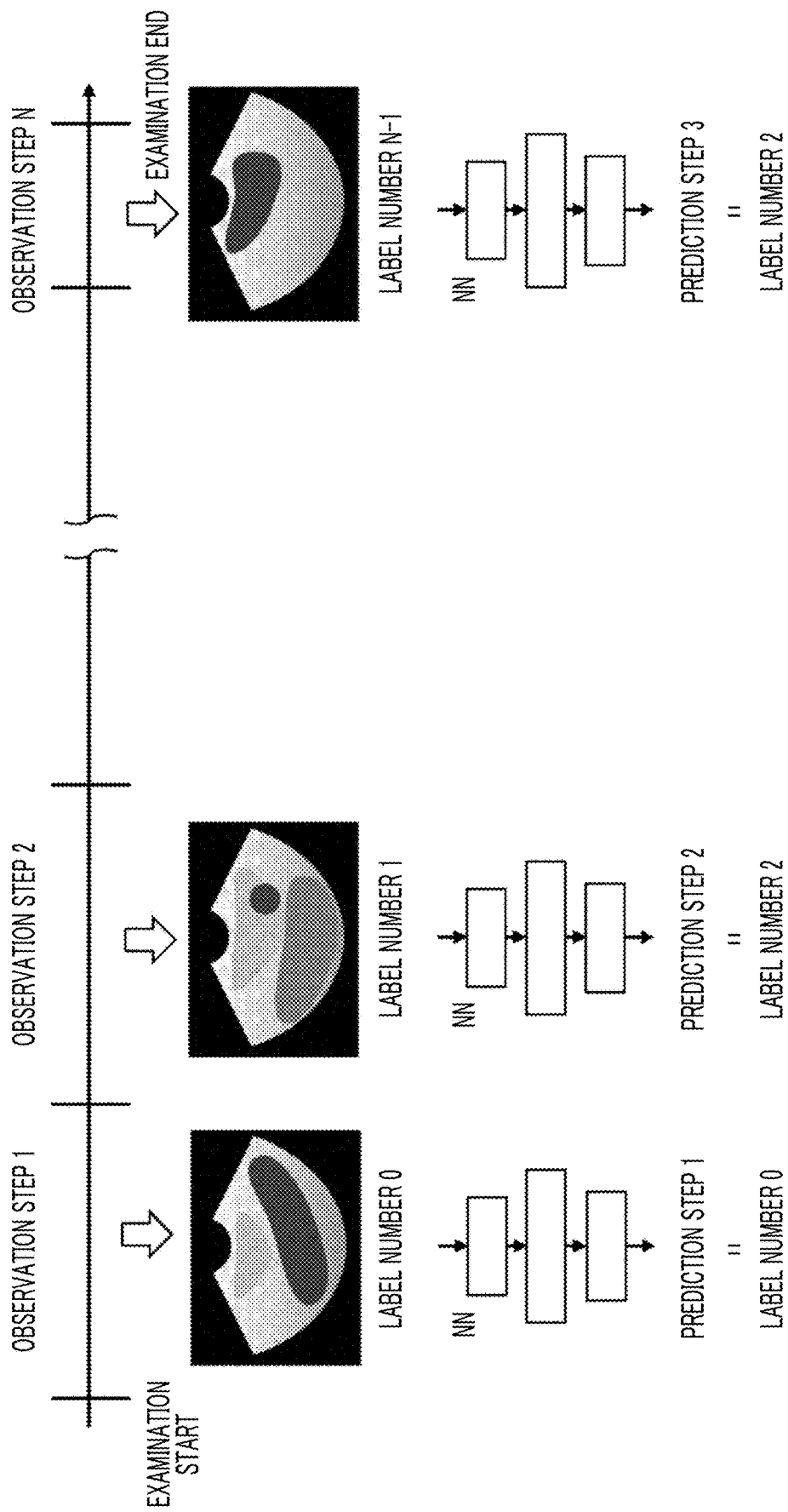
FIG. 8 is a conceptual diagram representing a flow from an examination start to an examination end of ultrasound diagnosis by the ultrasound endoscope system.

FIG. 8 is a conceptual diagram representing a flow from an examination start to an examination end of ultrasound diagnosis by the ultrasound endoscope system 10. FIG. 8 shows (N+1) observation steps 1, 2, . . . , and N (where N is an integer) from the examination start to the examination end. The observation steps 1, 2, . . . , and N represents an order from the examination start to the examination end of the ultrasound diagnosis, and ground truth steps corresponding to the observation steps 1, 2, . . . , and N are represented by label numbers 0, 1, . . . , and N−1.

In the observation step 1, an ultrasound image 1 of an observation target part 1 is acquired by the image acquisition unit. The ultrasound image 1 is displayed on the monitor 20 under the control of the display controller 172.

Subsequently, the label number 0 is output by the step prediction unit (NN) 112 as a prediction step 1 predicting an observation step corresponding to the ultrasound image 1 from the ultrasound image 1 based on the learning result.

The label number 0 of the prediction step 1 is displayed on the monitor 20 under the control of the display controller 172.

Subsequently, the label number 0 of the prediction step 1 is compared with a label number 0 of a ground truth step 1 corresponding to the prediction step 1 by the step comparison unit 116.

As a result, since a difference between the label number 0 of the prediction step 1 and the label number 0 of the ground truth step 1 is 0, learning by the step prediction unit 112 is not performed.

In the observation step 2, an ultrasound image 2 of an observation target part 2 is acquired by the image acquisition unit. The ultrasound image 2 is displayed on the monitor 20 under the control of the display controller 172.

Subsequently, the label number 2 is output by the step prediction unit 112 as a prediction step 2 predicting an observation step corresponding to the ultrasound image 2 from the ultrasound image 2 based on the learning result. The label number 2 of the prediction step 2 is displayed on the monitor 20 under the control of the display controller 172.

Subsequently, the label number 2 of the prediction step 2 is compared with a label number 1 of a ground truth step 2 corresponding to the prediction step 2 by the step comparison unit 116.

As a result, since a difference between the label number 2 of the prediction step 2 and the label number 1 of the ground truth step 2 is 1, the learning controller 118 makes the step prediction unit 112 learn a relationship between the ultrasound image and the prediction step based on a result of comparison such that the difference of 1 is close to 0.

Hereinafter, similarly, the above-described operation is repeated up to the observation step N.

In an initial stage of learning, the optimization of the learned model does not progress, and it is expected that the prediction step may significantly deviate from the ground truth step; however, as the optimization of the learned model progresses by learning, it can be expected that the prediction step becomes gradually close to the ground truth step.

In the ultrasound endoscope system 10, since information relating to the prediction step can be displayed on the monitor 20 in the middle of examination of ultrasound diagnosis, it is possible to allow the operator to reliably ascertain which part inside the body of the patient is observed at this moment.

As the related art, there is a technique (segmentation or detection) that recognizes a region or the like of a specific organ from an ultrasound image; however, in the ultrasound endoscope system 10, recognition of a region or the like of such an organ is not performed, an order of examination or an imaging period (section or time period) for imaging (observing) a specific observation target part is defined as an observation step, and only prediction about an observation step into which each ultrasound image is classified among a plurality of observation steps is performed.

In a case of organ recognition, such as segmentation, according to the related art, while a position and a region of an organ in an ultrasound image can be recognized, a lot of labor is needed for creating a ground truth step for one ultrasound image. In contrast, since the classification of the observation step by the ultrasound endoscope system 10 can be realized only by labeling an observation step to which each ultrasound image belongs, the classification of the observation step can be realized only with a little labor.

In a case where the step prediction unit 112 is constituted using the above-described convolutional neural network, the convolutional neural network may output, as a prediction step, a discrete probability distribution vector (hereinafter, simply referred to as a vector) that includes a plurality of elements representing a probability of an ultrasound image being an ultrasound image corresponding to each observation step or a scalar predicting a label number.

In a case of outputting a vector, the convolutional neural network outputs a plurality of elements corresponding to a plurality of observation steps in each observation step. The convolutional neural network outputs a vector that includes N elements representing a probability of an ultrasound image being an ultrasound image corresponding to each of the first to N-th observation steps 1 to N in the first observation step 1. The same applies to the second to N-th observation steps 2 to N.

Furthermore, a ground truth step is set as a discrete probability distribution vector where a probability of an element corresponding to an observation step, which is a ground truth, is 1 and a probability of an element corresponding to an observation step, which is not a ground truth, is 0.

In this case, a loss function represents a difference between a discrete probability distribution vector of a prediction step and a discrete probability distribution vector of a ground truth step. As the loss function, a softmax cross entropy, a sigmoid cross entropy, and the like are well used.

Furthermore, in a case of outputting a vector, a convolutional neural network may output a discrete probability distribution vector, in which a sum of probabilities of a plurality of elements is 1, using a softmax function as an activation function to be applied in an output final stage, or may output a discrete probability distribution vector representing a probability of each of a plurality of elements being a probability of each observation step using a sigmoid function.

The softmax function outputs a vector where the sum of the probabilities of a plurality of elements is 1.0=100%. That is, since the sum of the probabilities of all elements is 100%, the ultrasound image is necessarily classified into any one observation step. In a case of using the softmax function, the convolutional neural network can output an observation step corresponding to an element with a highest probability among a plurality of elements as a prediction step.

Subsequently, the sigmoid function outputs a vector representing a probability of each element alone being each observation step. Accordingly, in regard to an output of the sigmoid function, unlike the output of the softmax function, the sum of the probabilities of all elements is not always 100%, and for example, the probabilities of all elements may be 0%. With this, for example, in a case where an ultrasound image that has not been learned before is input to the convolutional neural network, it is possible to make determination that the ultrasound image is not classified into any observation step. Furthermore, in a case where there are a plurality of elements with a comparatively high probability, it is also possible to make determination that "a result has low reliability of recognition". In addition, in a case where the probabilities of elements corresponding to the third and fourth observation steps 3 and 4 are high, it is also possible to make determination that a position between the observation target part 3 and the observation target part 4 corresponding to the observation steps 3 and 4 is observed.

Figure 9:
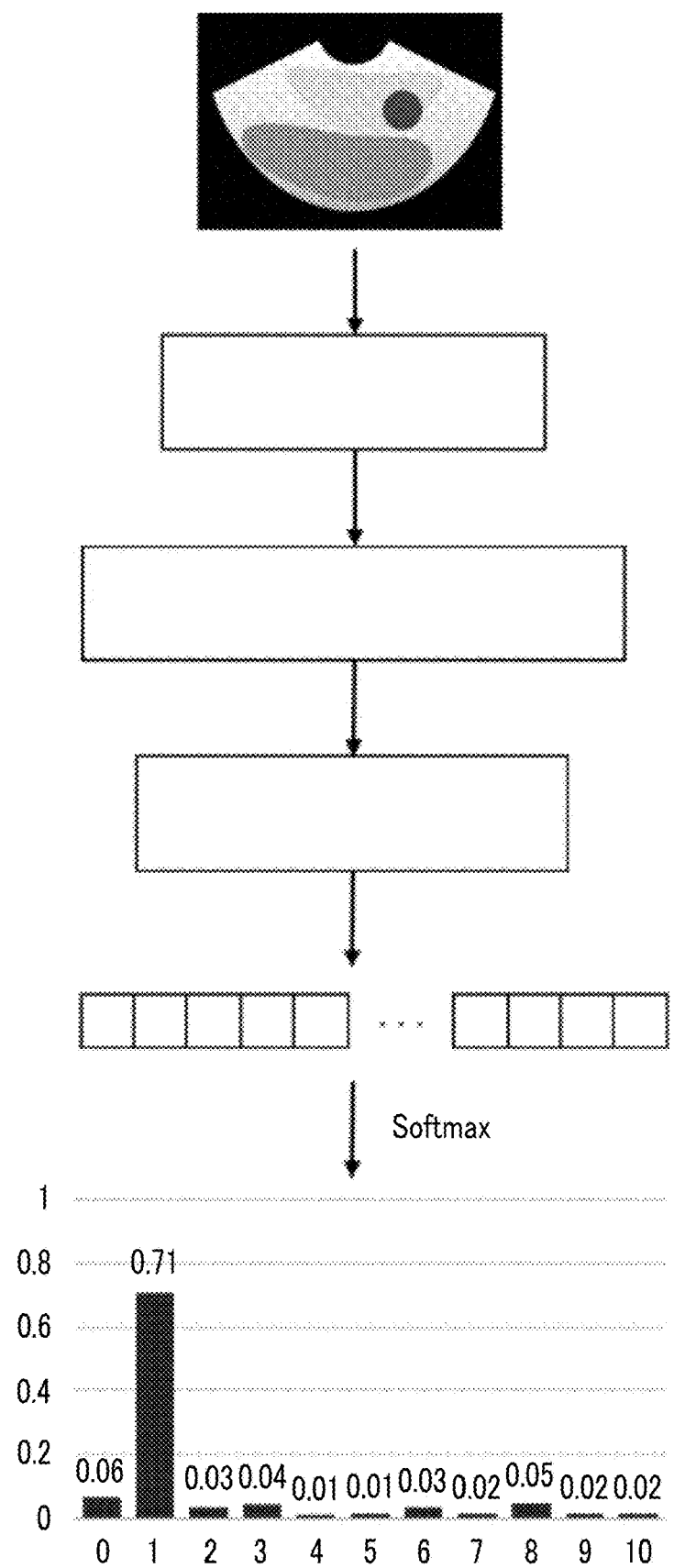
FIG. 9 is a conceptual diagram representing an output of a convolutional neural network using a softmax function.

FIG. 9 is a conceptual diagram showing the output of the convolutional neural network using the softmax function. The horizontal axis of a graph shown in a lower portion of FIG. 9 represents the label numbers 0 to 10 of the observation steps 1 to 11 corresponding to a plurality of elements included in the vector, and the vertical axis represents a probability of each of a plurality of elements being each of the observation steps 1 to 11 represented by the label numbers 0 to 10.

In the graph of FIG. 9, a probability of an element 1 corresponding to the first observation step 1 represented by the label number 0 is 0.06=6%, a probability of an element 2 corresponding to the second observation step 2 represented by the label number 1 is 0.71=71%, . . . . As shown in the graph, a vector where the sum of the probabilities of all elements is 1 is output from the convolutional neural network using the softmax function.

Figure 10:
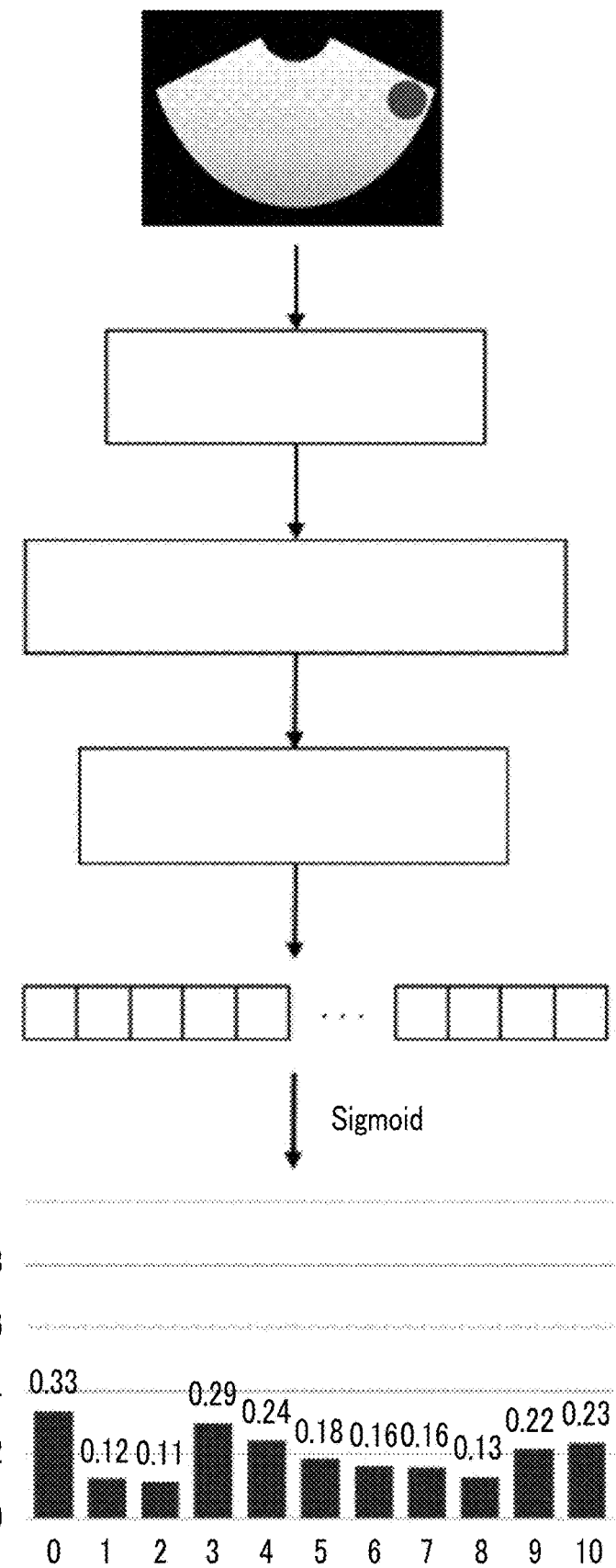
FIG. 10 is a conceptual diagram representing an output of the convolutional neural network using a sigmoid function.

Subsequently, FIG. 10 is a conceptual diagram representing the output of the convolutional neural network using the sigmoid function. The horizontal axis and the vertical axis of a graph in a lower portion of FIG. 10 are the same as in the case of the graph of FIG. 9.

In the graph of FIG. 10, a probability of the element 1 corresponding to the first observation step 1 represented by the label number 0 is 0.33=33%, a probability of the element 2 corresponding to the second observation step 2 represented by the label number 1 is 0.12=12%, . . . . As shown in the graph, a vector representing a probability of each of a plurality of elements being each observation step is output from the convolutional neural network using the sigmoid function.

On the other hand, in a case of outputting a scalar, in each observation step, the convolutional neural network outputs one prediction step predicting a label number corresponding to the observation step. In the first observation step 1, the convolutional neural network outputs a scalar predicting a label number corresponding to the first observation step 1 as a prediction step 1. The same applies to the second to N-th observation steps 2 to N.

Furthermore, a ground truth step is set to a scalar representing a label number.

In this case, the loss function represents a difference between the scalar of the prediction step and the scalar of the ground truth step. With this, it is possible to make the loss function interlocked with the difference between the label number of the prediction step and the label number of the ground truth step. As the loss function, a mean squared error (MSE), a mean absolute error (MAE), or the like is often used.

In a case where the convolutional neural network outputs a scalar, the label number of the prediction step predicting the label number corresponding to the observation step is not limited to an integer value, such as 0, 1, 2, . . . , and for example, a numerical value including a value below a decimal point, such as 2.1 or 2.2, may be output. In this case, the label number of the prediction step can be made an integer value by rounding off the value below the decimal point. Furthermore, in a case where the label number is changed from 2 to 3, such as from 2.1 to 2.2, determination can also be made that movement is made from the observation target part 2 corresponding to the observation step 2 to the observation target part 3 corresponding to the observation step 3.

For example, in normal image classification like classification of kinds of animals, while dog is a ground truth, in a case where cat is predicted and in a case where car is predicted, learning of the convolutional neural network is performed similarly.

In contrast, in a case of observation step classification, while the observation step 1 is a ground truth, in a case where the observation step 2 is predicted and in a case where the observation step 3 is predicted, the former is a "worthy" (close to a ground truth) error and the latter is an "unworthy" (far from a ground truth) error. Thus, in the latter case, there is a need to handle a greater amount of learning (amount of adjustment) of the convolutional neural network than in the former case.

Accordingly, as shown in Expression (1) described below, the loss function may perform weighting on an output L of the loss function based on a difference D between a label number of a prediction label and a label number of a ground truth label and may output a weighted output L'. That is, the loss function adjusts the output L of the loss function to be greater in a case where the difference D is greater than a threshold value Dth (unworthy) than in a case where the difference D is smaller than the threshold value Dth (worthy). The greater the output L' of the loss function is, the greater the amount of learning (amount of adjustment) of the convolutional neural network becomes.

$$Dth>D, L'=\alpha L$$

$$Dth \leq D, L'=\beta L \qquad \text{Expression 1}$$

Here, $\alpha<\beta$.

In this way, the observation step, the prediction step, and the ground truth step are represented by the label number, and the label number is set based on the observation order of the observation target part, whereby it is possible to include information that the label number of the prediction step is close to the label number of the ground truth step (worthy) and that the label number of the prediction step is far from the label number of the ground truth step (unworthy), in the output of the loss function. For this reason, it is possible to reflect such information in learning of the convolutional neural network, and to more efficiently perform learning.

A plurality of observation steps may include an observation step representing a state in which any observation target part is not imaged (observed). In this case, the observation step representing the state in which any observation target part is not imaged (observed) is provided, whereby it is also possible to recognize an observation step representing, for example, a state before an examination start or after an examination end of ultrasound diagnosis. Furthermore, in a case where an ultrasound image of an unexpected part, an ultrasound image of which the entire surface is black, or the like is captured, it is possible to give a warning representing that the observation step is unclear, or the like.

The invention is not limited to the ultrasound endoscope system 10 of the above-described embodiment, and can be applied to medical equipment that acquires a medical image of an observation target part inside a body of a subject in each of a plurality of observation steps in which an observation order of the observation target part is determined.

The image acquisition unit may be equipment that acquires a medical image inside a body of a subject captured from the outside of the body of the subject, for example, an in-vitro ultrasound apparatus or the like. Alternatively, equipment that is inserted into a body cavity of the subject and acquires a medical image inside the body of the subject captured from the inside of the body of the subject, for example, an endoscope apparatus that captures an endoscope image, an ultrasound endoscope apparatus that captures an endoscope image and an ultrasound image, or the like can be exemplified. Furthermore, the image acquisition unit may be a part that acquires a medical image from medical equipment, such as an in-vitro ultrasound apparatus, an endoscope apparatus, or an ultrasound endoscope apparatus, or a medical image management system (Picture Archiving and Communication Systems (PACS)) that saves and manages medical images of subjects captured by various kinds of medical equipment, or the like.

Although the learning device of the invention has been described in connection with a case where the learning device is incorporated in the ultrasound endoscope system, the learning device of the invention can also be similarly incorporated in various kinds of medical equipment other than the ultrasound endoscope system. Alternatively, the learning device of the invention may not be incorporated in the medical equipment, and may be provided separately from the medical equipment.

Furthermore, the medical image is not particularly limited as long as an image is captured by the medical equipment, and for example, an endoscope image, an ultrasound image, and the like can be exemplified. In addition, as the ultrasound image, an ultrasound image in which an observation target part inside a body of a subject is imaged by an ultrasound endoscope, or the like can be exemplified.

In the device according to the embodiment of the invention, for example, the hardware configurations of the processing units that execute various kinds of processing, such as the step prediction unit 112, the step comparison unit 116, the learning controller 118, the display controller 172, and the console 100, may be dedicated hardware or may be various processors or computers that execute programs. Furthermore, the hardware configuration of the ground truth step holding unit 114 may be dedicated hardware or may be a memory, such as a semiconductor memory.

Various processors include a central processing unit (CPU) that is a general-purpose processor executing software (program) to function as various processing units, a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like.

One processing unit may be configured of one of various processors described above or may be configured of a combination of two or more processors of the same type or different types, for example, a combination of a plurality of FPGAs, a combination of an FPGA and a CPU, or the like. Furthermore, a plurality of processing units may be configured of one among various processors or may be configured using one processor obtained by combining two or more of a plurality of processing units.

For example, as represented by a computer, such as a server or a client, there is a form in which one processor is configured of a combination of one or more CPUs and software, and the processor functions as a plurality of processing units. For example, as represented by system on chip (SoC) or the like, there is a form in which a processor that implements all functions of a system including a plurality of processing units into one integrated circuit (IC) chip is used.

In addition, the hardware configuration of various processors is, more specifically, an electric circuit (circuitry), in which circuit elements, such as semiconductor elements, are combined.

For example, a method according to the embodiment of the invention can be implemented by a program that causes a computer to execute respective steps. Furthermore, it is possible to provide a computer-readable recording medium having the program recorded thereon.

Although the invention has been described above in detail, the invention is not limited to the above-described embodiment, and various improvements and alterations may be of course made without departing the spirit and scope of the invention.

EXPLANATION OF REFERENCES

10: ultrasound endoscope system
12: ultrasound endoscope
14: ultrasound observation device
16: endoscope processor
18: light source device
20: monitor
21a: water supply tank
21b: suction pump
22: insertion part
24: operating part
26: universal cord
28a: air and water supply button
28b: suction button
29: angle knob
30: treatment tool insertion port
32a: ultrasound connector
32b: endoscope connector
32c: light source connector
34a: air and water supply tube
34b: suction tube
36: ultrasound observation portion
38: endoscope observation portion
40: distal end portion
42: bending portion
43: flexible portion
44: treatment tool lead-out port
45: treatment tool channel
46: ultrasound transducer unit
48: ultrasound transducer
50: ultrasound transducer array
54: backing material layer
56: coaxial cable
60: FPC
74: acoustic matching layer
76: acoustic lens
82: observation window
84: objective lens
86: solid-state imaging element
88: illumination window
90: cleaning nozzle
92: wiring cable
100: console
112: step prediction unit
114: ground truth step holding unit
116: step comparison unit
118: learning controller
140: multiplexer
142: reception circuit
144: transmission circuit
146: A/D converter
148: ASIC
150: cine memory
151: memory controller
152: CPU
154: DSC
158: pulse generation circuit
160: phase matching unit
162: B mode image generation unit
164: PW mode image generation unit 166: CF mode image generation unit
168: ultrasound image recognition unit
172: display controller

What is claimed is:

1. A learning device comprising:
a processor, configured to:
   acquire a medical image of an observation target part inside a body of a subject in each of a plurality of observation steps in which an observation order to examine the observation target part is determined, wherein each of the plurality of observation steps represents an order set based on the observation order of the observation target part;
   output a prediction step being an observation step predicted from the medical image based on a learning result in each of the plurality of observation steps;
   hold a ground truth step corresponding to each of the plurality of observation steps, wherein the ground truth step represents an observation step of a ground truth corresponding to the medical image in each of the plurality of observation steps;
   compare the prediction step with the ground truth step corresponding to the prediction step in each of the plurality of observation steps; and
   make a neural network learn a relationship between the medical image and the prediction step based on a result of comparison in each of the plurality of observation steps such that a difference between the prediction step and the ground truth step is minimized in each of the plurality of observation steps,
wherein each of the plurality of observation steps, the plurality of prediction steps, and the plurality of ground truth steps is represented by a label number, and
wherein in each of the plurality of observation steps, the neural network outputs a scalar predicting the label number as the prediction step, and the ground truth step is a scalar representing the label number.

2. The learning device according to claim 1,
wherein the label number is set based on the observation order of the observation target part.

3. The learning device according to claim 1,
wherein the neural network is a convolutional neural network using a loss function, and
wherein in each of the plurality of observation steps, the processor makes the convolutional neural network learn the relationship between the medical image and the prediction step such that an output of the loss function calculated based on a difference between the label number of the prediction step and the label number of the ground truth step is minimized.

4. The learning device according to claim 3,
wherein in each of the plurality of observation steps:
   the loss function represents a difference between the scalar of the prediction step and the scalar of the ground truth step.

5. The learning device according to claim 4,
wherein the loss function adjusts the output of the loss function to be greater in a case where the difference is greater than a threshold value than in a case where the difference is smaller than the threshold value.

6. The learning device according to claim 1,
wherein the plurality of observation steps include an observation step representing a state in which any observation target part is not observed.

7. The learning device according to claim 1,
wherein, in a case where the processor observes the medical image of the observation target part inside the body of the subject in compliance with the observation order of the observation target part, each of the plurality of observation steps represents an order set based on the observation order of the observation target part.

8. The learning device according to claim 1,
wherein the medical image is acquired by an equipment configured to be inserted into a body cavity of the subject, and wherein the equipment is configured to capture the medical image from inside the body of the subject.

9. The learning device according to claim 1,
wherein the medical image is an ultrasound image.

10. The learning device according to claim 9,
wherein the medical image is the ultrasound image in which the observation target part inside the body of the subject is imaged by an ultrasound endoscope.

11. A learning method comprising:
acquiring a medical image of an observation target part inside a body of a subject in each of a plurality of observation steps in which an observation order to examine the observation target part is determined, wherein each of the plurality of observation steps represents an order set based on the observation order of the observation target part;
outputting a prediction step being an observation step predicted from the medical image based on a learning result in each of the plurality of observation steps;
comparing the prediction step with a ground truth step corresponding to the prediction step in each of the plurality of observation steps, wherein the ground truth step represents an observation step of a ground truth corresponding to the medical image in each of the plurality of observation steps; and
making a neural network learn a relationship between the medical image and the prediction step based on a result of comparison in each of the plurality of observation steps such that a difference between the prediction step and the ground truth step is minimized in each of the plurality of observation steps,
wherein each of the plurality of observation steps, the plurality of prediction steps, and the plurality of ground truth steps is represented by a label number, and
wherein in each of the plurality of observation steps, the neural network outputs a scalar predicting the label number as the prediction step, and the ground truth step is a scalar representing the label number.

12. A processor configured to:
a learn the relationship between the medical image and the prediction step in each of the plurality of observation steps by the learning method according to claim 11 and output the prediction step predicting the observation step corresponding to the medical image from the medical image based on a learning result in each of the plurality of observation steps.

* * * * *